US012644736B2

(12) United States Patent
Armsworthy et al.

(10) Patent No.: US 12,644,736 B2
(45) Date of Patent: Jun. 2, 2026

(54) FREE SURFACE FLOW MEASUREMENT ASSEMBLY

(71) Applicant: Flo Sciences, LLC, Los Angeles, CA (US)

(72) Inventors: Frank Graydon Armsworthy, Morrisville, NC (US); William Kevin Carpenter, Morrisville, NC (US); Nathan Thomas Spalding Maher, Morrisville, NC (US); Devin Sloane, Los Angeles, CA (US); Carson Westra, Los Angeles, CA (US); Hilario Pinedo, Valencia (ES); Alberto Compte, Valencia (ES); Julia Jimenez, Valencia (ES); Francisco Plaza, Valencia (ES); Julio Caro Silva, Valencia (ES); Celia Perez Salla, Valencia (ES); Ricardo Londono Cano, Valencia (ES); Christopher Geyer, Los Angeles, CA (US)

(73) Assignee: FLO SCIENCES, LLC, Los Angeles, CA (US)

( * ) Notice: Subject to any disclaimer, the term of this patent is extended or adjusted under 35 U.S.C. 154(b) by 0 days.

(21) Appl. No.: 19/323,852

(22) Filed: Sep. 9, 2025

(65) Prior Publication Data

US 2026/0071903 A1 Mar. 12, 2026

Related U.S. Application Data

(60) Provisional application No. 63/692,496, filed on Sep. 9, 2024.

(51) Int. Cl.
*A61B 5/20* (2006.01)
*G01F 1/00* (2022.01)
(Continued)

(52) U.S. Cl.
CPC ................. *G01F 1/58* (2013.01); *A61B 5/208* (2013.01); *G01F 1/007* (2013.01); *G01F 15/14* (2013.01)

(58) Field of Classification Search
CPC . A61B 5/208; G01F 1/007; G01F 1/52; G01F 1/56; G01F 1/58; G01F 1/584
See application file for complete search history.

(56) References Cited

U.S. PATENT DOCUMENTS

| | | | | |
|---|---|---|---|---|
| 3,859,854 A | * | 1/1975 | Dye | A61B 5/208 73/215 |
| 3,871,231 A | * | 3/1975 | Ciarico | A61G 9/006 600/584 |

(Continued)

FOREIGN PATENT DOCUMENTS

| | | | | |
|---|---|---|---|---|
| DE | 102014008760 B4 | 3/2019 | | |
| WO | WO-9201420 A1 | * | 2/1992 | G01F 1/007 |

(Continued)

OTHER PUBLICATIONS

International Search Report and Written Opinion issued in PCT/US2025/045616.

*Primary Examiner* — Herbert K Roberts
(74) *Attorney, Agent, or Firm* — Jeffer Mangels & Mitchell LLP; Brennan C. Swain, Esq.

(57) ABSTRACT

A flow measurement device for assessing free surface fluid flow that includes a void container defining a void chamber and including an upper opening configured to receive the free surface fluid flow, a measurement container defining a measurement chamber in fluid communication with the void chamber via at least one through opening, an exit orifice defined in the measurement container and configured to allow fluid to drain from the measurement chamber at a known outflow rate based on fluid level, and at least one capacitive sensor configured to measure a level of fluid in
(Continued)

the measurement chamber. A fluid path is defined through the upper opening, into the void chamber, through the at least one through opening, into the measurement chamber, and through the exit orifice.

5 Claims, 19 Drawing Sheets

(51) Int. Cl.
   *G01F 1/52*      (2006.01)
   *G01F 1/58*      (2006.01)
   *G01F 15/14*     (2006.01)

(56)               References Cited

U.S. PATENT DOCUMENTS

| | | | | |
|---|---|---|---|---|
| 4,100,802 | A * | 7/1978 | Layton | G01F 5/00 |
| | | | | 600/584 |
| 4,241,017 | A * | 12/1980 | Balistreri | G01F 19/00 |
| | | | | 600/580 |
| 5,176,148 | A * | 1/1993 | Wiest | A61B 5/208 |
| | | | | 600/573 |
| 6,324,906 | B1 * | 12/2001 | Rinkewich | G01F 1/52 |
| | | | | 73/816 |
| 11,536,649 | B1 | 12/2022 | Yan | |
| 2003/0130808 | A1 * | 7/2003 | Kapitulskiy | G01F 11/284 |
| | | | | 702/45 |
| 2011/0000309 | A1 * | 1/2011 | Griffiths | G01F 23/266 |
| | | | | 73/861.08 |
| 2011/0166537 | A1 * | 7/2011 | Paulen | A61B 5/208 |
| | | | | 604/318 |
| 2015/0105694 | A1 * | 4/2015 | Mahajan | G01F 9/003 |
| | | | | 600/584 |
| 2017/0105670 | A1 | 4/2017 | Holt | |
| 2019/0008439 | A1 | 1/2019 | Sageder et al. | |
| 2020/0205717 | A1 | 7/2020 | Yang | |
| 2022/0192567 | A1 * | 6/2022 | Hidas | G01F 23/241 |
| 2024/0108264 | A1 | 4/2024 | Minze | |

FOREIGN PATENT DOCUMENTS

| | | | | |
|---|---|---|---|---|
| WO | WO-9324052 | A1 * | 12/1993 | G01F 23/62 |
| WO | WO-2023128873 | A2 * | 7/2023 | A61B 5/208 |

* cited by examiner

FREE SURFACE FLOW MEASUREMENT ASSEMBLY

CROSS-REFERENCE TO RELATED APPLICATIONS

This application claims the benefit of U.S. Provisional Application No. 63/692,496, filed on Sep. 9, 2024, the entirety of which is incorporated by reference herein.

FIELD OF THE INVENTION

The present invention relates to urinary flow measurement and, in particular, a portable free surface flow measurement assembly.

BACKGROUND OF THE INVENTION

Prior art urinary flow systems or devices typically include review of results by a doctor or upload of the data for processing, which results in the user not receiving feedback or results until a later period of time. Also, many prior art devices must remain static during use (e.g., they have to be placed on a surface and then the user voids into the device). These drawbacks make it difficult for users to take urinary flow measurements at home. The present invention addresses the issues discussed above.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a flow measurement device for assessing free surface fluid flow that includes a void container defining a void chamber and including an upper opening configured to receive the free surface fluid flow, a measurement container defining a measurement chamber in fluid communication with the void chamber via at least one through opening, an exit orifice defined in the measurement container and configured to allow fluid to drain from the measurement chamber at a known outflow rate based on fluid level, and at least one capacitive sensor configured to measure a level of fluid in the measurement chamber. A fluid path is defined through the upper opening, into the void chamber, through the at least one through opening, into the measurement chamber, and through the exit orifice.

The flow measurement device may include a diverter positioned in the void chamber above the at least one through opening to prevent direct entry of fluid into the at least one through opening and isolate the measurement chamber from splashing or turbulence in the void chamber. The diverter may be angled at between about 40 degrees and about 65 degrees relative to a top surface of the device. The flow measurement device may include an overflow container defining an overflow chamber in fluid communication with the void chamber via an overflow opening positioned to receive excess fluid when a capacity of the void chamber and measurement chamber is exceeded. The device may also include a spout in fluid communication with both the exit orifice and an exit of the overflow chamber, with the exit of the overflow chamber positioned above or at a level higher than the exit orifice.

The one or more capacitive sensors may be arranged on a measurement wall that at least partially defines the measurement chamber. The measurement wall may include a coating layer on an inner surface thereof to insulate the capacitive sensor from fluid while allowing capacitive measurement through the coating layer. The conformal coating layer may comprise a polyimide material with low absorption properties. The flow measurement device may include an outer housing enclosing the void container and measurement container, and a handle pivotally attached to the outer housing and movable between a stowed position and a deployed position to position the device at a predetermined hang angle during use. The predetermined hang angle is essentially any angle where the vertical axis of the device is not perpendicular to the horizon or the bottom surface when the device is positioned on a horizontal surface. In a preferred embodiment, the predetermined hang angle positions a top surface of the device at an angle between about 9.5 degrees and about 49.5 degrees relative to horizontal. The device may include at least one of an inclinometer, gyroscope, or accelerometer configured to detect the hang angle and adjust volume calculations based on device orientation, including roll, pitch or yaw. In a preferred embodiment, the top surface of the outer housing is not parallel to a bottom surface of the outer housing, defining a top slope angle therebetween of between about 1 degrees and about 20 degrees, with the preferred angle being 7 degrees.

The flow measurement device may include indicators configured to provide feedback on flow rate, such as a light ring around the upper opening displaying colors indicative of flow quality. The exit orifice may be vertically oriented and have a rectangular shape with a width between about 0.1 mm and about 2 mm and a height between about 10 mm and about 40 mm to provide resolution at low flow rates. The exit orifice may have a non-rectangular shape with a narrower width at a bottom portion or surface than at a top portion or surface to accommodate higher flow rates. The non-rectangular exit orifice may be selected from V-shaped, T-shaped or trapezoid shaped. The void chamber may be funnel-shaped with a taper from a larger cross-section at the upper opening to a smaller cross-section at a bottom thereof.

The device may include a vent at a top of the measurement chamber to allow air escape. The processor may be configured to compute the inflow rate Z as $Z=X-Y$, where X is a rate of change in measured volume (dV/dt), Y is the known outflow rate as a function of fluid volume V, and V is an instantaneous fluid volume in the device adjusted for device geometry and orientation. The device may include a main printed circuit board operatively connected to the plurality of sensors and the processor for processing raw sensor data into volume measurements and flow rates. The measurement chamber may be positioned laterally adjacent to the void chamber, and the void container and measurement container share a common wall.

In accordance with another aspect of the present invention there is provided a method of measuring free surface fluid flow using a flow measurement device that includes directing a free surface fluid flow into a void chamber of the device through an upper opening, allowing the fluid to flow from the void chamber into a measurement chamber in fluid communication with the void chamber via at least one through opening, measuring a level of fluid in the measurement chamber over time using at least one sensors, draining fluid from the measurement chamber through an exit orifice at a known outflow rate based on the fluid level, and calculating an inflow rate of the free surface fluid flow based on a rate of change in fluid volume derived from the measured fluid level and the known outflow rate. The method may include positioning the flow measurement device at a predetermined hang angle, wherein the predetermined hang angle positions a top surface of the device at an angle between about 9.5 degrees and about 49.5 degrees relative to horizontal. Positioning the device at the predetermined hang angle may include moving a handle pivotally attached to an outer housing of the device from a stowed position to a deployed position and holding the handle to allow the device to hang at the predetermined hang angle. This may be based on the interaction of the handle with angled stop surfaces on the housing. The method may include detecting the hang angle using at least one of an inclinometer, gyroscope, or accelerometer, and adjusting the fluid volume calculations based on the detected hang angle, including compensation for roll, pitch, or yaw.

The method may include directing excess fluid from the void chamber into an overflow chamber via an overflow opening when a capacity of the void chamber and measurement chamber is exceeded, thereby invalidating the measurement if overflow occurs, and draining fluid from the overflow chamber and the exit orifice into a common spout, wherein fluid from the overflow chamber enters the spout above the exit orifice to maintain laminar flow from the exit orifice. The method device may include directing drained fluid from the device into a commode, wherein the device acts as an intermediary between a user's bladder and the commode. The method may include diverting the fluid in the void chamber using a diverter positioned above the at least one through opening to prevent direct entry of fluid into the at least one through opening and isolate the measurement chamber from splashing or turbulence. The free surface fluid flow is preferably urinary flow, and the calculating step further comprises determining an instantaneous inflow rate and a total volume of a urination event. The exit orifice may be vertically oriented and rectangular, and the known outflow rate is calibrated based on the geometry of the exit orifice and the fluid level.

The method may include providing real-time feedback on the inflow rate via indicators on the device, such as a light ring displaying colors indicative of flow quality, and/or calculating the inflow rate Z comprises computing $Z = X - Y$, where X is a rate of change in measured volume (dV/dt), Y is the known outflow rate as a function of instantaneous fluid volume V, and V is adjusted based on geometries of the void chamber and measurement chamber and device orientation. The method may also include taking multiple fluid level measurements at intervals as short as 0.05 seconds to generate a flow rate curve over time. The method may include processing raw data from the sensors using a processor to convert capacitance counts to fluid volume based on chamber geometries and device orientation.

In accordance with another aspect of the present invention there is provided a battery door assembly for the flow measurement device or that can be used with other handheld devices. The battery door assembly includes a housing defining a battery compartment configured to receive at least two batteries in a side-by-side orientation with parallel axes. The at least two batteries are configured to be inserted in an axial direction. The battery door assembly also includes a battery door configured to cover the battery compartment, the battery door including a plurality of tabs and an inner surface perpendicular to the axes of the at least two batteries, a plurality of tab receivers defined in the housing and configured to receive the plurality of tabs, a gasket positioned between the battery door and the housing and sealing against the inner surface of the battery door to provide a waterproof seal, and a fastener configured to secure the battery door to the housing and compress the gasket.

The plurality of tabs may include three lower tabs and two upper tabs, and the plurality of tab receivers includes three lower tab receivers and two upper tab receivers. The plurality of tabs may include lower tabs and upper tabs positioned at different levels on the battery door, wherein the upper tabs are positioned at a level above a lower end of the at least two batteries. The battery door assembly may include channels defined in the housing adjacent the lower tab receivers, where the lower tabs are configured to be inserted into the channels and slid into the lower tab receivers during assembly. The housing may include a gasket trough, and the gasket is positioned in the gasket trough and seals against the inner surface of the battery door. The fastener is preferably a threaded fastener extending through a first fastener opening in the battery door and into a second fastener opening in the housing. When the handheld device is a flow measurement device the battery door assembly may be positioned on a bottom of the housing adjacent a spout.

The battery door assembly may include a battery spring mounted on the inner surface of the battery door, the battery spring being configured to contact the at least two batteries and provide an electrical connection. The battery door may include a spring receiving platform on the inner surface thereof, and the battery spring is mounted on the spring receiving platform. The battery door may include one or more weep holes configured to allow moisture to escape. The battery compartment is configured to receive two batteries in the side-by-side orientation with parallel axes. The battery door assembly may include a grip pad member on a bottom of the housing, the grip pad member at least partially surrounding a spout of the handheld device to protect the spout from contact with a surface. The housing may include a battery flange member defining a door recess configured to receive the battery door.

The present invention is directed to a free surface flow measurement device or assembly that measures instantaneous or virtually instantaneous flow rate (e.g., measure in in cc/sec or mL/sec) and total volume (e.g., measured in cc or mL) of a void or expelling event where free surface flow prevents use of a more conventional flowmeter. It will be appreciated that free surface flow is the gravity driven flow of a fluid under a free surface, for example water flowing under air in the atmosphere. In a preferred embodiment, the device is used for measuring urination events (which is a free surface flow), but this is not a limitation on the present invention. Generally, fluid is directed, at an unpredictable flow rate, into a container that includes a calibrated or known release, leak, exit opening, exit slot or the like. In a preferred embodiment, the exit opening is a vertical slot. Liquid or fluid exiting through the exit opening behaves differently at low volumes. This allows good resolution of measurement at low flow rates, especially at the beginning or end of a void event. The fluid or liquid accumulates in the container and a portion escapes or exits via the exit opening. The volume of the liquid in the container is measured continuously via capacitive sensors. The capacitive sensors (also called liquid level sensors) may measure fluid volume through counts, with calibrated relationships between sensor counts and actual volume in the measurement and void chambers (as a combined chamber). The rate-of-change of that liquid volume allows instantaneous flow rate to be calculated as the arithmetic difference between the measured change in volume and the computed exit flowrate, which is a function of instantaneous level. The method used to measure instantaneous volume may be include: mass, volume is dependent on density, level, volume is independent of density, capacitive, resistive, laser time-of-flight, ultrasonic time-of-flight.

The free surface flow measurement device may include an electronic inclinometer to detect deviations from measured or assumed level. This, in turn, permits on-the-fly corrections in measured volume and, therefore, instantaneous flow rate. In a preferred embodiment, the internal geometry of the container includes a labyrinthine arrangement to isolate a column of fluid within a separate volume, space or chamber from where the fluid enters the device. The separate volume or chamber allows the column of fluid or liquid to be isolated from waves, foam, and/o splashing that may occur in the space or volume where the free surface flow stream enters. The internal geometry may also include geometry that provides or acts as a controlled overflow, preventing fluid from exceeding the capacity of the measurement device. It will be appreciated that at any point in time during use, the device is or may be computing or determining: instantaneous fluid volume in the device, which may be designated herein as "V", rate-of-change of the measured volume in the device (dV/dt), which may be designated herein as "X", flow-rate exiting the device, as a nonlinear function of V, which may be designated herein as "Y", and volumetric flow rate of the input stream, which is X-Y and may be designated herein as "Z". Generally, the computation of flow rate may include a two-chamber flow path (i.e., the void chamber and the measurement chamber) and a Z=X–Y approach (inflow=dV/dt minus calibrated outflow as a function of level).

The device, or versions thereof, may be used by people at home, at doctor's or medial offices, in the field (e.g., in a third world country), at clinics. There also may be different version, such as a consumer version, professionals version (e.g., for doctor's) and an on the go version (in the field). It will be appreciated that the device is essentially an intermediary in the flow of urine between a user's bladder and the toilet or commode. This prevents someone from having to urinate into a container to determine a flow rate and then pour the urine into the toilet. In its simplest form, the present invention is a container with a calibrated release, leak or exit slot therein, where free surface flow is directed into the container and where the level or volume in the container is measured on an almost continuous basis to determine the rate of change of the fluid flow (e.g., in cubic centimeters per second). Preferably two parameters, the rate of change of the fluid within the measurement container or chamber and the rate at which fluid is draining out of the measurement container or chamber, are being determined or measured as virtually continuously or at least as quickly as every few milliseconds. The rate at which fluid is draining out of the measurement container can be determined because the geometry or dimensions of the exit slot or leak are known. It will be appreciated that the speed at which the fluid is draining from the exit slot is variable and depends on the height or level of the fluid in the measurement chamber. The rate of change of fluid in the measurement chamber minus calculated leakage or exit of fluid out of the measurement chamber is approximately equal to the volumetric flow rate of the free surface flow fluid (e.g., urine) that is being directed into the container. An embodiment is discussed herein where the measurement chamber and main chamber (the chamber through which the free surface flow fluid enters) are separate. However, in another embodiment, the main chamber and the measurement chamber are the same.

In a preferred embodiment, the present invention includes a free surface flow measurement assembly that includes a main container that includes a main chamber and an upper opening, a measurement container that defines a measurement chamber, where the main chamber is in flow communication with the measurement chamber via at least one through holes, wherein the measurement container includes an exit slot defined in a sidewall thereof, and a spout. The exit slot is in fluid communication with the spot, and a fluid path is defined through the upper opening, into the main chamber, through the at least one through hole, into the measurement chamber, through the exit slot and out of the spout. The main container may define a main container interior, where at least a portion of the measurement container is positioned within the main container interior, and at least a portion of the measurement container defines the main chamber. The free surface flow measurement assembly may include a first measurement device associated with the measurement container, where the first measurement device is configured to determine the level of fluid located in the measurement chamber.

The present invention is directed to a device or assembly for quantifying, measuring or otherwise assessing free surface fluid flow, and, in particular, urinary flow. In a preferred embodiment, the present invention is a free surface flow measurement assembly that includes a main container having a main container interior, a main chamber and an upper opening. The assembly also includes a measurement container that defines a measurement chamber. Preferably, the measurement container (and the measurement chamber) is at least partially exposed in the main container interior. In another embodiment, the measurement container (and the measurement chamber) may be disposed outside of the main container interior. One or more, and preferably two, through openings or holes are positioned at or near the bottom of the main chamber so that the main chamber is in flow communication with the measurement chamber. The measurement container includes at least one exit slot defined in a sidewall thereof. A fluid path may be defined through the upper opening, into the main chamber, through the at least one through hole, into the measurement chamber, through the exit slot and out of a spout positioned at the bottom of the main container.

In an exemplary use, fluid enters the main container and flows into the main, receiving or void chamber of the assembly through the upper opening. The main container is preferably a funnel and includes a taper, such that the main chamber includes a larger cross-section at the top and a smaller cross-section at the bottom. Fluid accumulates in the main chamber. The main chamber is connected to or in fluid communication with the measurement chamber via one or more through openings or holes at or near the bottom of the main chamber. As the fluid accumulates in the main chamber, as a result of the fluid communication with the measurement chamber, a measurement column or volume of fluid accumulates in the measurement chamber. It will be appreciated that hydrostatic pressure forces the level in the measurement chamber or measurement column and that in the main chamber to be at or nearly identical or level.

In a preferred embodiment, one or more electronic sensors continuously monitors the level of the measurement column in the measurement chamber. For example, a capacitive sensor may be used, however, this is not a limitation and other types of level-sensors may be used. The sidewall of the main container may include an elongated slot defined therein and a portion of the measurement container may include a measurement wall that at least partially defines the measurement chamber. With this arrangement, the sensor(s) and the related PCB(s), etc. may be positioned outside of the main container and may be associated with or have access to the measurement chamber.

The measurement chamber includes the exit slot at or near the bottom thereof. During use, fluid from the measurement chamber continuously drains out of the exit slot. In another embodiment, the exit slot may be located in or at the bottom of the main chamber. It will be appreciated that the shape of exit slot is important to resolution, accuracy, and precision and low flow rates. For example, in a preferred embodiment, the exit slot may have width of between about 0.1 mm and a height of about 40 mm or a width of between about 0.5 mm and a height of about 25 mm, or a width of between about 1 mm and a height of about 20 mm, or a width of between about 2 mm and a height of about 10 mm. Any range within the above ranges is also within the scope of the present invention. Any area calculation within these ranges is also within the scope of the present invention. For example, the area of a 20 mm×1 mm orifice is 20 mm2. Fluid that has exited the exit slot then drains from a spout or any opening (which may be directly from the exit slot) that is preferably shaped to direct the fluid out of the device or assembly and into a commode or the like. It will be appreciated that the dimensions above can be scaled up. For example, the device may be used for more than just urine flow measurement. Other free surface flows may be measured and the size of the exit orifice, together with the geometry/volume of the measurement and void containers/chambers can be scaled up together such that they are at the same proportion.

In a preferred embodiment, the device may include an overflow chamber that is defined within an overflow tube. In use, should a combination of high flow-rate and/or excessive duration exceed the capacity of the main chamber, the overflow tube is provided to direct the excess through an overflow opening in the top of the overflow tube and to the spout. The measurement chamber can also include an overflow opening at the top thereof. It should be noted that any entry of fluid into the overflow tube through the overflow opening would compromise or invalidate the test, as the overflow would not be registered by the sensor. It will be appreciated that if overflow is required, then the drain pipe or overflow tube may be integrated in such a way that overflow fluid exits upstream or downstream of the exit slot restriction.

The measurement container may be essentially three sidewalls within the main container that cooperate with the measurement wall to define the measurement chamber. The measurement wall may be any object that at least partially contains the fluid in the measurement chamber. The sensor may be sized to allow measurement of the column of fluid in the measurement chamber at any desired level. Preferably, the sensor includes a plurality of zones (e.g., twenty vertical or vertically staggered zones) that help identify the level of the fluid. For example, the sensor may include two columns of zones that overlap left and right. With this arrangement (and with enough zones) there will always be one zone where the fluid level is at or near the middle half of that zone. Then, it can be determined which zone has the highest likelihood of the fluid level being located in that zone. For example, if it is determined that the fluid level is at a higher percentage chance than other zones, then the other zones are ignored. The wall and sensor may be held in position by a frame.

It will be appreciated that the main container interior is defined by the side wall(s) of the main container and the main chamber is the volume into which fluid that enters through the upper opening collects, but is separate from the measurement chamber 16 and the overflow chamber (other than any fluid that may enter the overflow tube). The overflow tube may be positioned adjacent the measurement container so fluid that passes through the exit slot and fluid that passes through the overflow chamber exit a common spout. In another embodiment, fluid from the overflow and the exit slot may exit the assembly separately or may be contained in common or separate spaces.

It will be appreciated that at any point in time during use, the device is or may be computing or determining: instantaneous fluid volume in the device, which may be designated herein as "V", rate-of-change of the measured volume in the device (dV/dt), which may be designated herein as "X", flow-rate exiting the device, as a nonlinear function of V, which may be designated herein as "Y", and volumetric flow rate of the input stream, which is X-Y and may be designated herein as "Z".

An ergonomic embodiment of the free surface flow measurement assembly may include a housing that includes or encompasses the components discussed herein. The assembly may include a handle so that a user can hold the device while urinating. The assembly may also include indicators or lights that may provide further information regarding the results of a test. For example, a light ring around the top of the upper opening may be green to indicate great flow, yellow to indicate moderate flow, red to indicate unhealthy flow or blue to show the device is in standby mode. Any colors, lights or locations of the lights or other indicators are within the scope of the present invention. These indicators and the numbers associated with great, moderate, unhealthy flow, etc. may be based upon known medical assessments or calculations.

It will be appreciated that the present invention may provide feedback to the user in real time (while they are using the device). The present invention is portable and can be used where the user is holding the device over a toilet, the flow is measured in real time, and the urine exits the bottom of the device and into the toilet. Device operates as a pass-through system, differentiating from traditional methods. Basic calculation formula: Flow Rate In=(Change in Volume/Time)+Flow Rate Out. Nomogram profiles (which may be shown in the related app) indicate clinical utility, displaying normal versus abnormal flow patterns critical for diagnosis and treatment assessments. The measured outflow numbers or calculations may be compared to normative or known data to establish if flow rates are considered normal, an issue, good, bad, etc. Inclinometer and orientation sensors allow real-time adjustments for accurate readings despite device positioning changes during use.

The commercial versions of the device may include a consumer version for home use and a professional version for clinical settings, which will cater to different market needs while retaining core technology. The pro version can replace traditional in-clinic machines, facilitating patient use outside examination rooms and enhancing operational efficiency in clinics. Other potential market applications include feasibility for field use in emerging markets, emphasizing the importance of portability in resource-limited settings.

The device also includes a waterproof battery door assembly. One of the advantages of the battery door assembly is that it seals a compartment that includes at least two batteries in a side-by-side configuration where the batteries are axially parallel and are oriented generally perpendicular to the battery door or the inner surface of the battery door that the gasket seals against. This battery door assembly or battery compartment assembly can be used on any device that need a waterproof or water resistant compartment while being able to insert the batteries end first into the compartment.

DETAILED DESCRIPTION OF THE PREFERRED EMBODIMENTS

Figure 1:
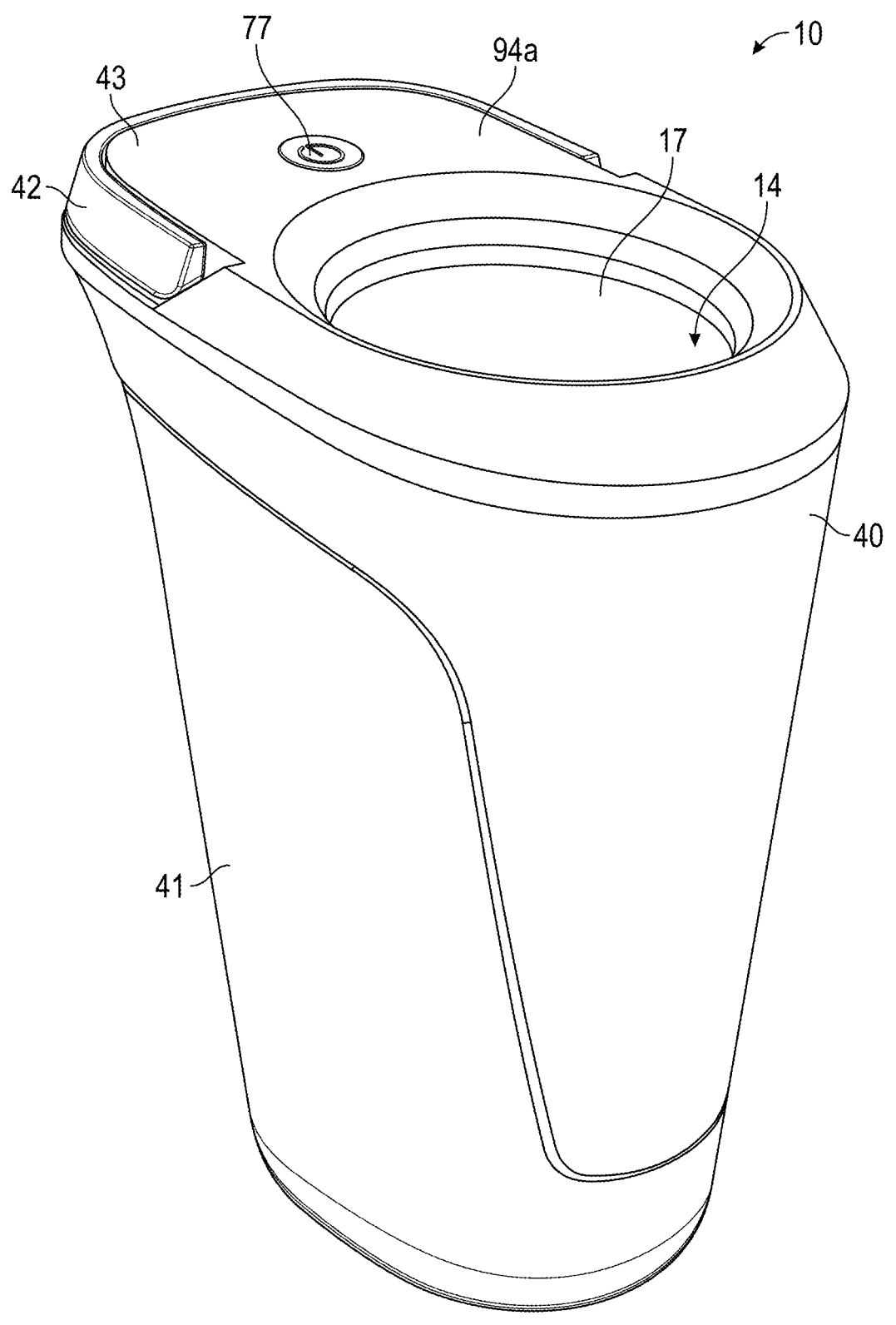
FIG. 1 is a perspective view of a flow assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Figure 2:
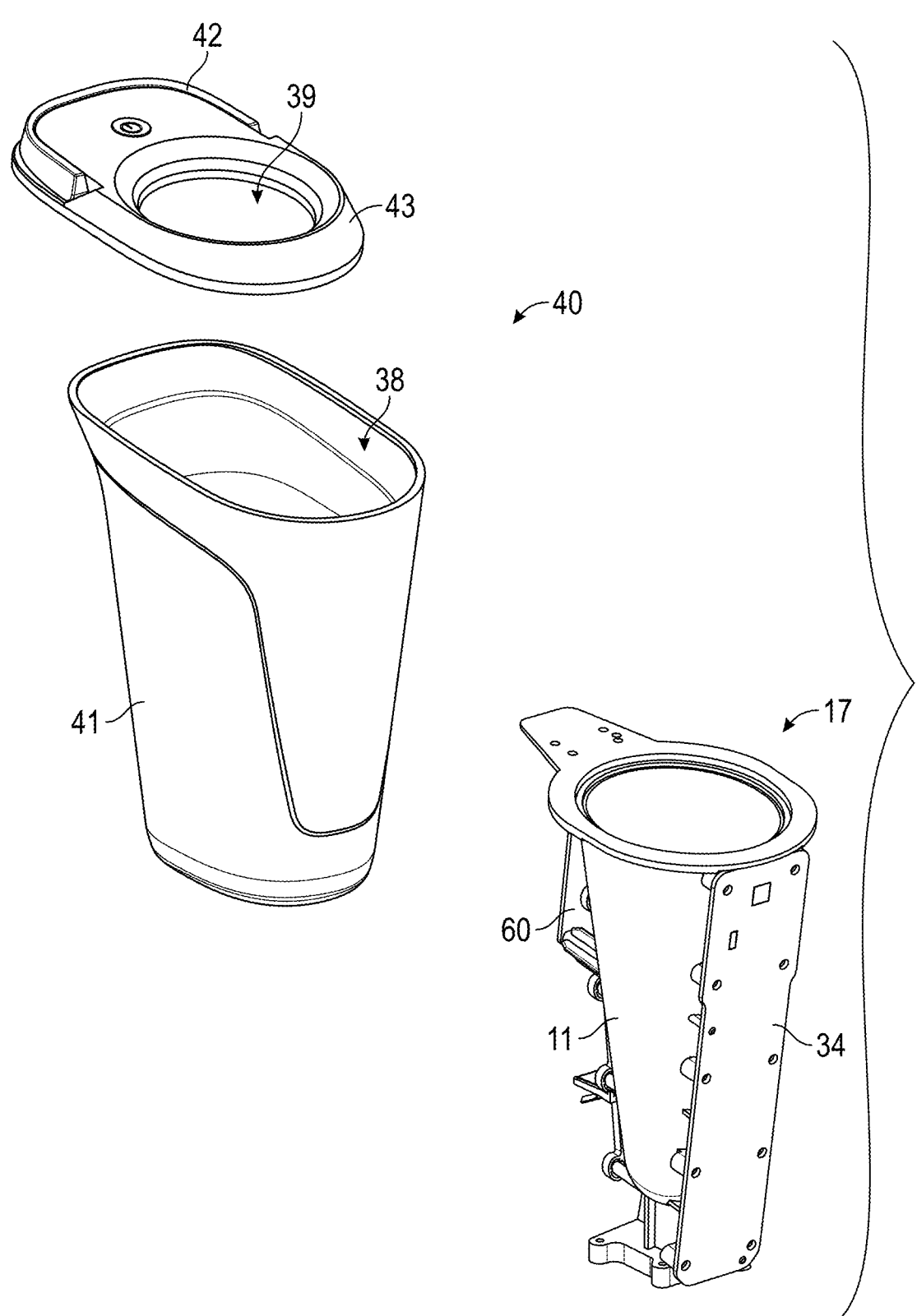
FIG. 2 is an exploded perspective view of the flow assembly.

With reference to FIGS. 1-18, the present invention is directed to a device or assembly for quantifying, measuring or otherwise assessing free surface fluid flow, and, in particular, urinary flow. As shown in FIGS. 1-2, in a preferred embodiment, the present invention includes a free surface flow measurement assembly, flow measurement device or flow assembly 10 that includes an interior or measurement assembly 17. The measurement assembly 17 may be disposed or contained within a housing interior 38 of an outer housing 40. As shown in FIG. 2, the outer housing 40 may include a main body portion 41, a cover portion 43 and a handle 42.

Figure 3:
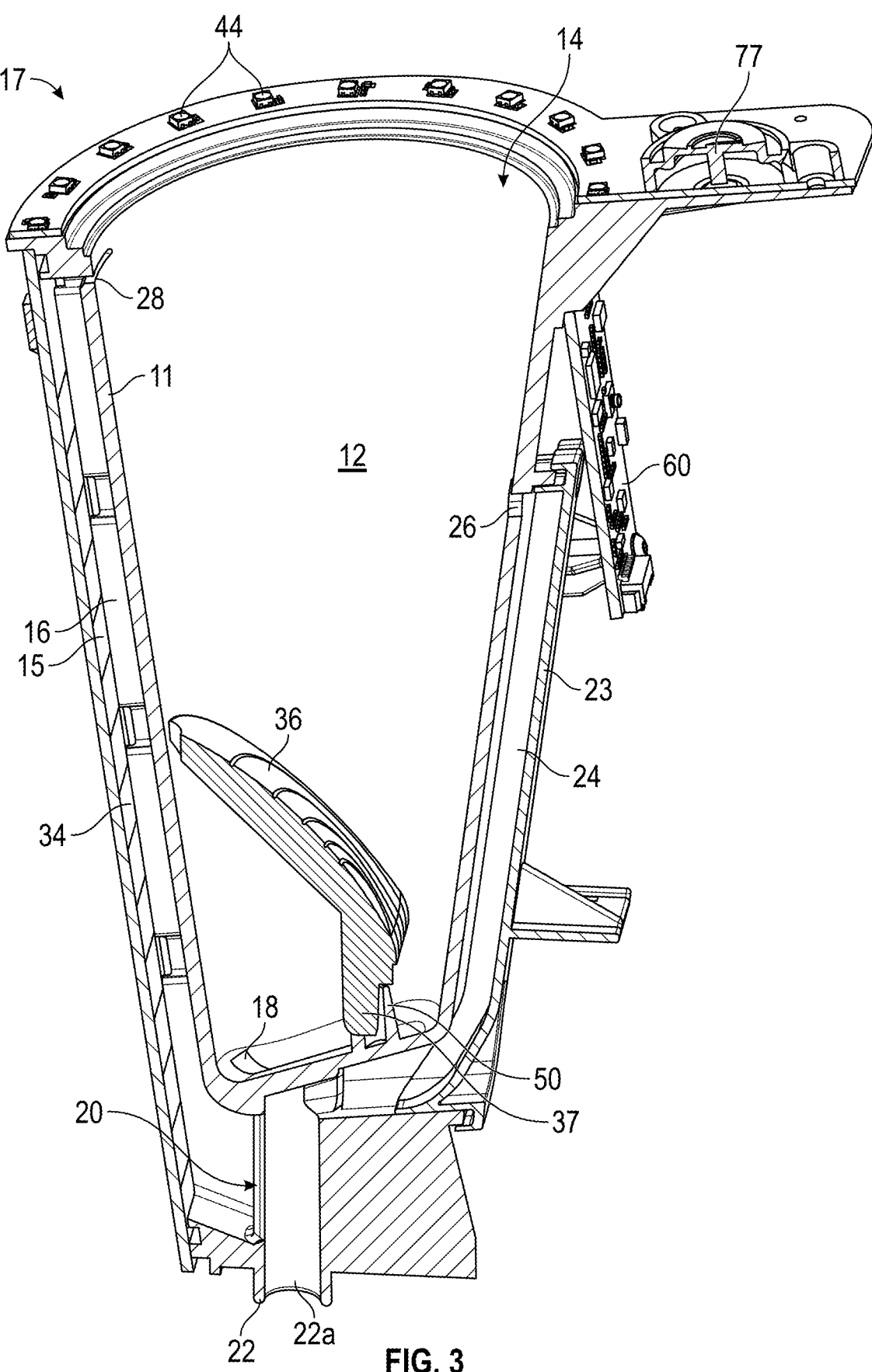
FIG. 3 is a cross-sectional perspective view of the measurement assembly.

FIGS. 3-7 show the measurement assembly 17 alone. In a preferred embodiment, the measurement assembly 17 includes a main body portion 52 (shown as a unitary piece in FIG. 6) that includes a main or void container 11 that defines a main or void chamber 12 and an upper opening 14 through which a user may urinate as an upper portion thereof, and a bottom section 25 that is positioned or extends below the void container 11. The upper opening 14 coincides or is aligned with an opening 39 in the cover portion 43 (see FIG. 2). The measurement assembly 17 also includes a measurement container 15 that defines a measurement chamber 16. As shown in FIG. 3, the measurement chamber 16 is positioned generally laterally adjacent to the void chamber 12. One or more, and preferably two, through openings or holes 18 are positioned at or near the bottom of the void chamber 12 so that the void chamber 12 is in flow communication with the measurement chamber 16. The measurement container 15 and measurement chamber 16 includes at least one exit slot or orifice 20 defined therein and preferably in a sidewall thereof that provides flow communication to a spout 22 through which the fluid exits the device. It will be appreciated that the term container is used to denote or include the walls of the void, measurement, overflow or other containers and the term "chamber" is used to denote or include the interior or negative space defined by the walls of the void, measurement, overflow or other containers. It will be appreciated that the void, measurement, overflow or other containers may share walls. For example, as shown in FIG. 3, the void and measurement containers share a wall and that wall partially defines the void chamber 12 on side and the measurement chamber 16 on the other side.

Figure 6:
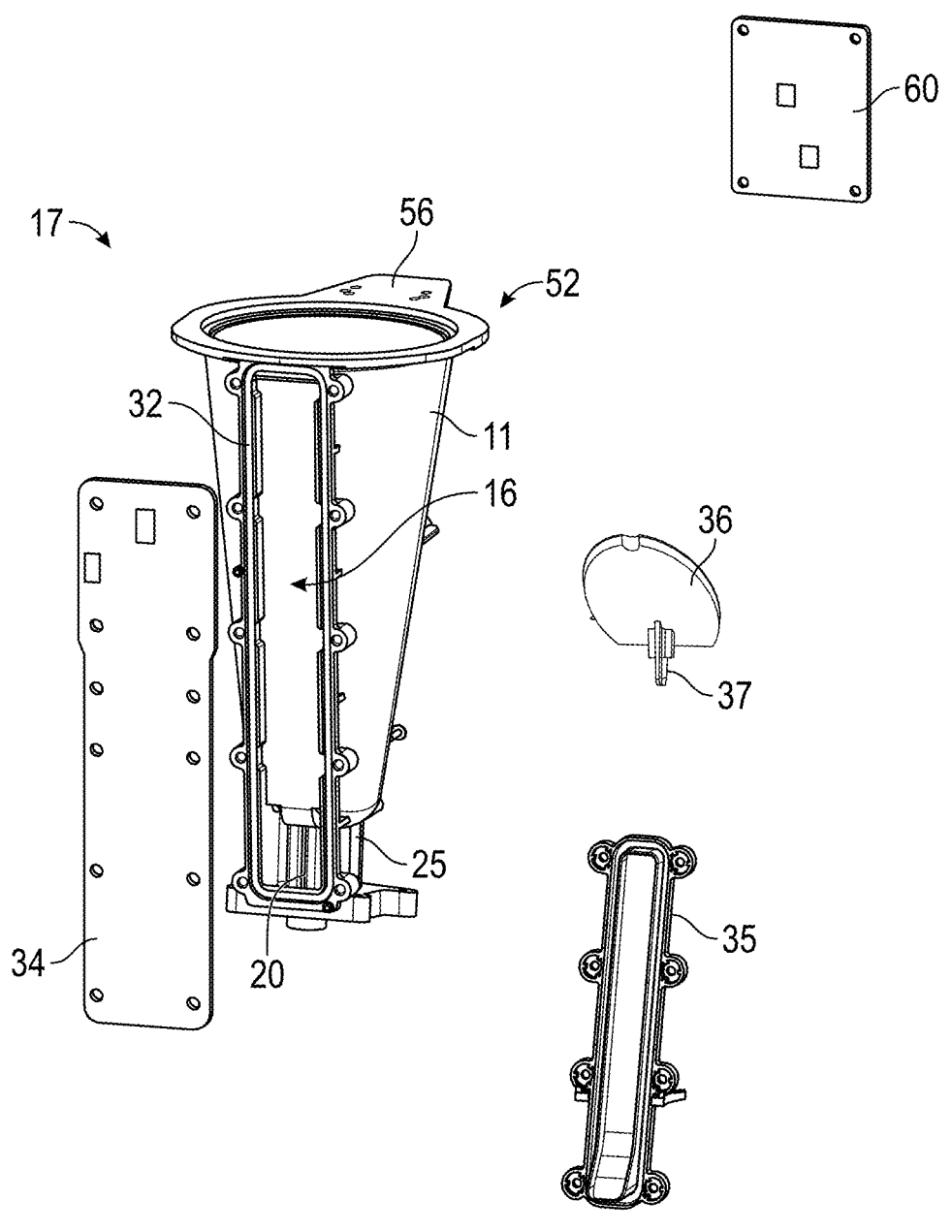
FIG. 6 is an exploded perspective view of the measurement assembly with the container member showing the open measurement chamber.
Figure 7:
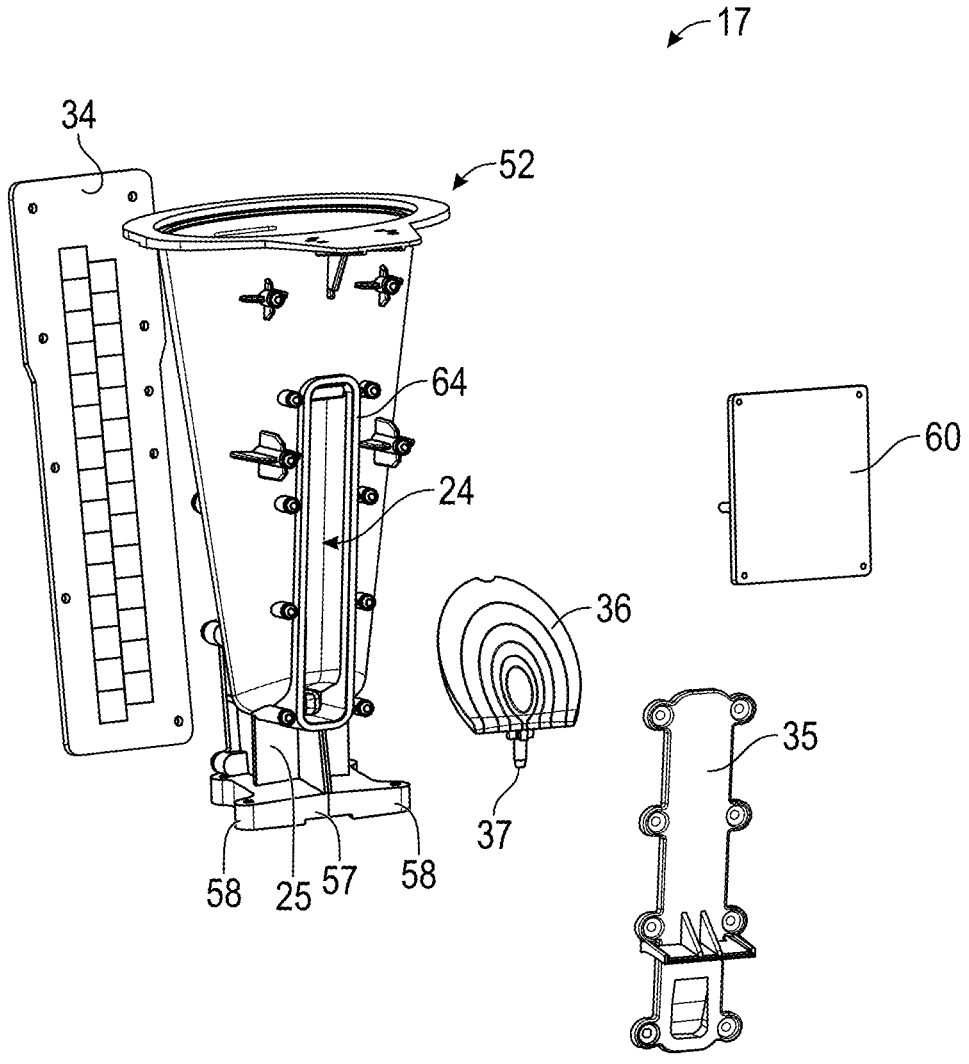
FIG. 7 is an exploded perspective view of the measurement assembly with the container member showing the open overlow chamber.

In a preferred embodiment, the measurement assembly 17 includes a container member or main body portion 52 that includes the void container 11 and at least partially defines the void chamber 12, measurement chamber 16 and overflow chamber 24 (described below). The main body portion 52 may be a unitary piece (as shown in FIGS. 6 and 7) and includes the bottom section 25 that extends below the void container 11. The bottom section 25 may include components for securing the measurement assembly 17 within the housing interior 38 and to the outer housing 40. As shown in FIG. 6, the bottom section 25 of the main body portion 52 includes a base 57 with a plurality of feet 58 that include mounting holes 54 therein. Threaded fasteners may extend through the bottom of the housing 40 and through or into the mounting holes 54 to secure the measurement assembly 17 to the housing 40. The main body portion 52 may also include an arm 56 (see FIG. 6), to which the PCB or PCBs for the button 77 and lights 44 may be secured.

As shown in FIGS. 6-7, in a preferred embodiment, the measurement assembly 17 includes a measurement wall 34, overflow cover 35, a main PCB 60 and a diverter 36. The main PCB 60 may control any portion of the electronics of the device. The main PCB 60 may include two harnesses that connect the main PCB to the measurement PCB or measurement wall 34 and the LED PCB. Power may also be connected to the main PCB. The measurement wall 34 is secured to a rectangular extension wall 62 that extends outwardly from the void container 11. The measurement wall 34, rectangular extension wall 62 and void container 11 together form the measurement container 15 and at least partially define the measurement chamber 16.

Figure 4:
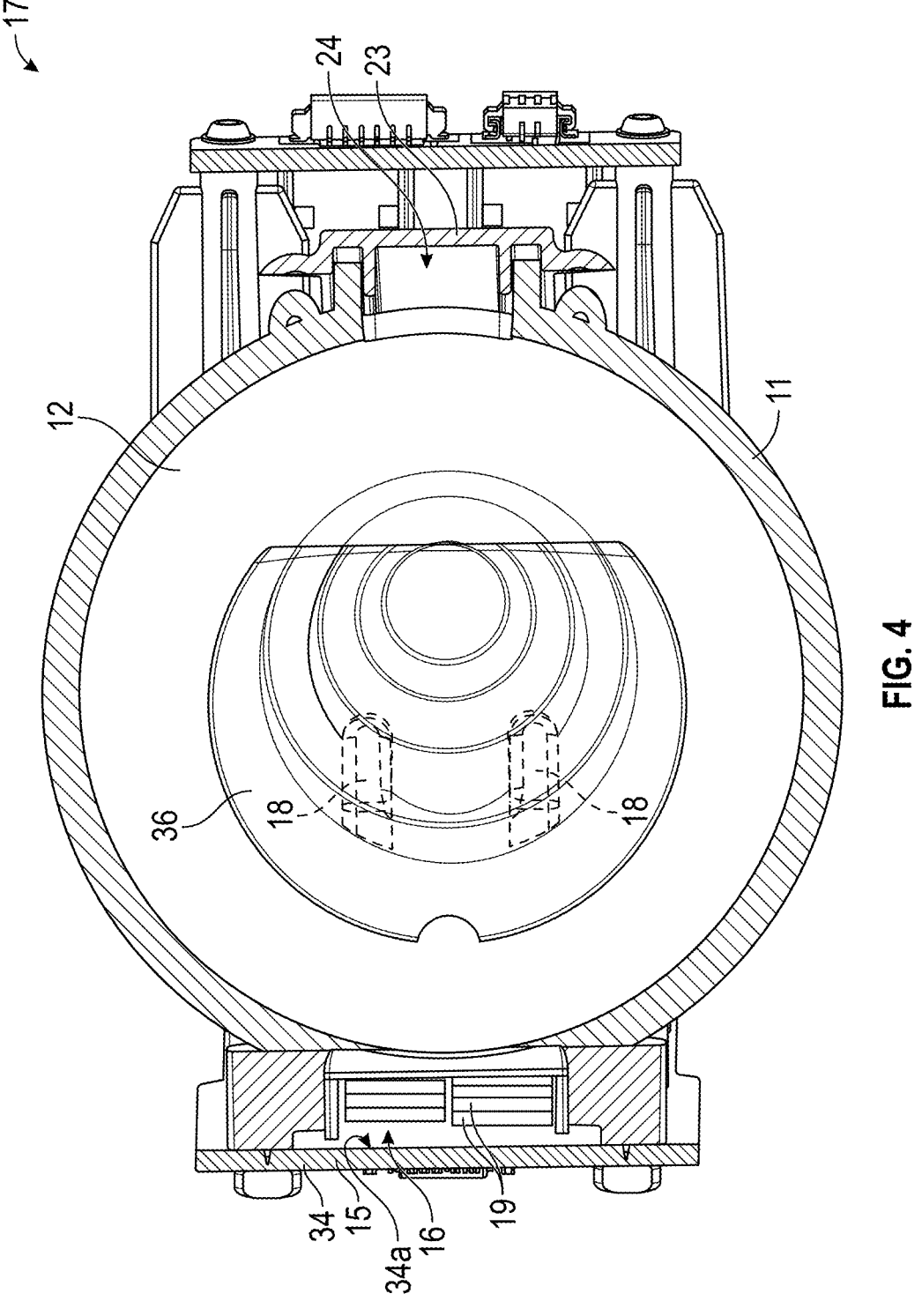
FIG. 4 is a cross-sectional elevational view of the measurement assembly.

As is shown in FIGS. 3-4, the diverter 36 is disposed in the void chamber 12. The purpose of the diverter 36 is to prevent the fluid that enters the void chamber 12 from entering the through holes 18 at the bottom of the void container 11 and affecting the flow measurement. The diverter 36 is preferably angled, as shown in FIG. 3. The diverter angle corresponds with the hang angle, which is described further below. The diverter 36 may define an angle (e.g., the diverter angle) of about 52 degrees to the top surface of the housing. The diverter angle may be between about 40 degrees and about 65 degrees. The diverter acts as a mechanical baffle. The diverter 36 may include a diverter extension 37 that is secured to or received in a connection member 50 on the bottom of the void container 11. Any method of securing or positioning the diverter 36 within the void chamber 12 to cover or protect the holes 18 is within the scope of the present invention.

Figure 8:
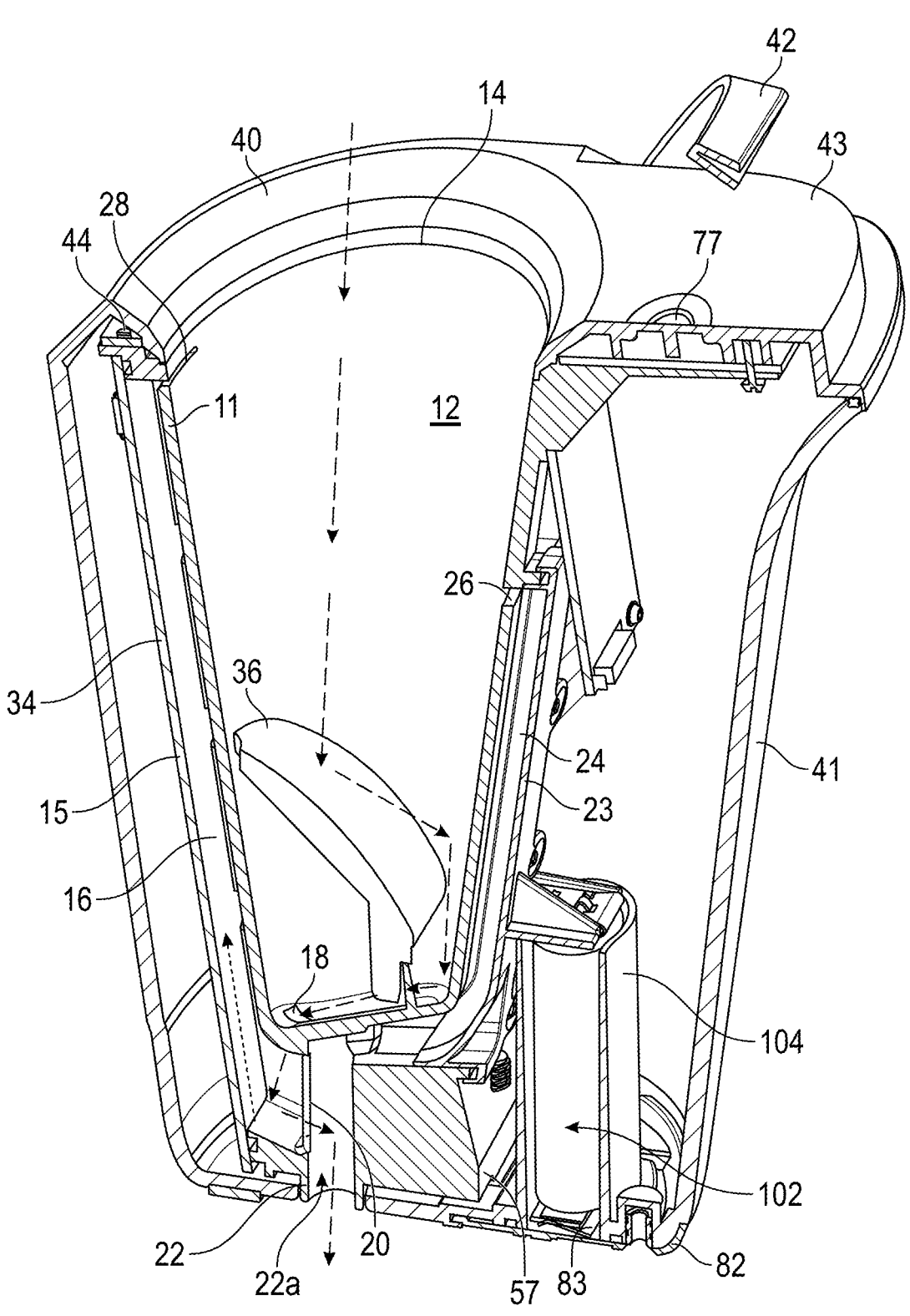
FIG. 8 is a cross-sectional perspective view of the flow assembly that shows an exemplary flow path.

As shown in FIG. 8, a fluid path is defined through the upper opening 14, into the void chamber 12, passed or against the diverter 36 (some fluid may contact the diverter, other fluid may go directly to the bottom surface of the void container 11), through the at least one through hole 18, into the measurement chamber 16, through the exit orifice 20 and out of the spout 22. This exemplary flow path is shown in FIG. 8 using dashed line arrows. It will be appreciated that, in use, the device may be positioned at a hang angle, as described below, as the fluid follows the fluid path and a flow rate measurement is taken.

In use, during a void event, fluid enters the void container 11 and into the void chamber 12 of the measurement assembly 17 through the upper opening 14. The void container 11 is preferably a funnel and includes a taper, such that the void chamber 12 includes a larger cross-section at the top and a smaller cross-section at the bottom. However, this is not a limitation and the taper may be omitted. During a void event, fluid accumulates in the void chamber 12. As shown in FIG. 8, the void chamber 12 is connected to or in fluid communication with the measurement chamber 16 via the one or more through openings or holes 18 at or near the bottom of the void chamber 12. As the fluid accumulates in the void chamber 12, as a result of the fluid communication with the measurement chamber 16, a measurement column or volume of fluid accumulates in the measurement chamber 16 (this is represented by the arrow with small dashes pointing upwardly in FIG. 8).

Figure 9:
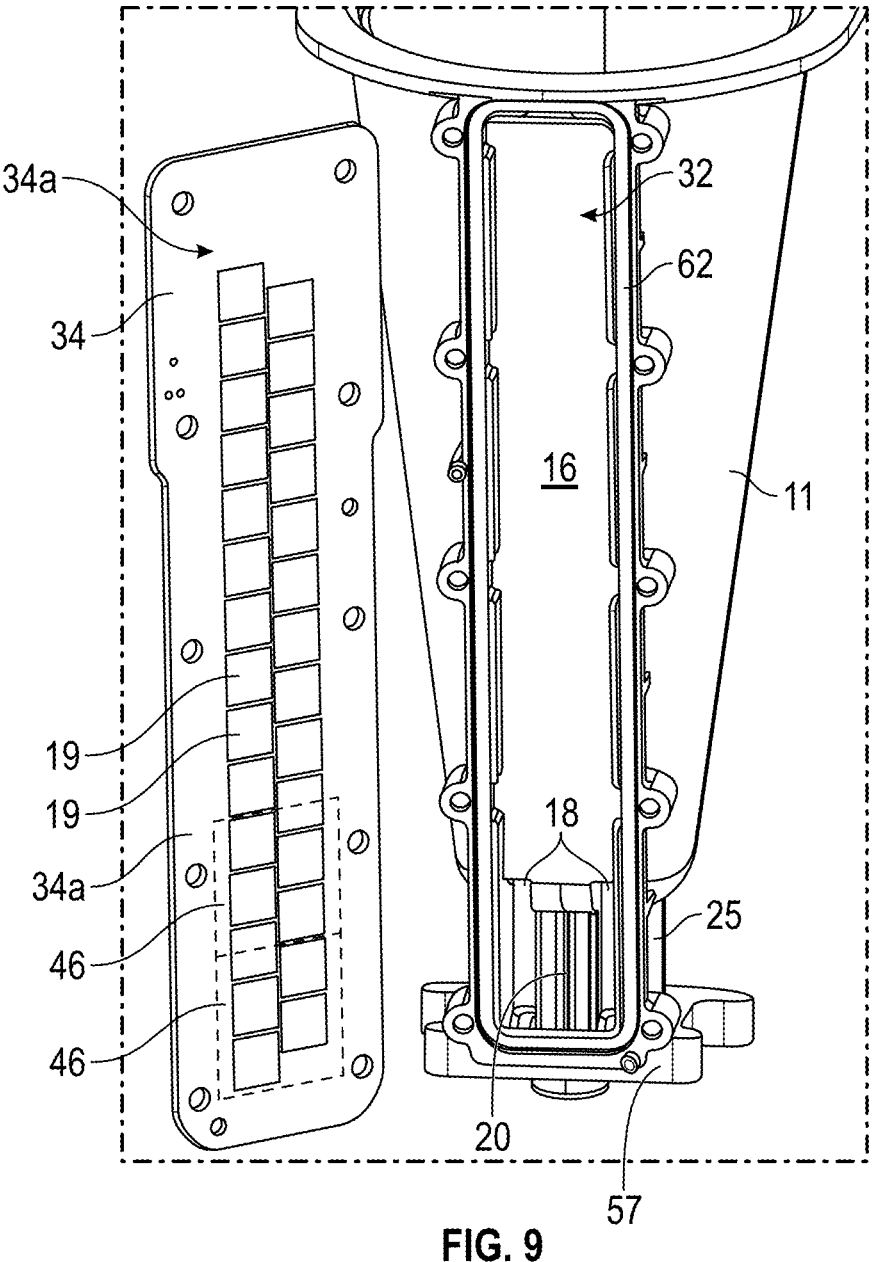
FIG. 9 is an exploded perspective view showing the measurement wall exploded off of the rectangular extension wall and rotated to show the array of sensors thereon.
Figure 10:
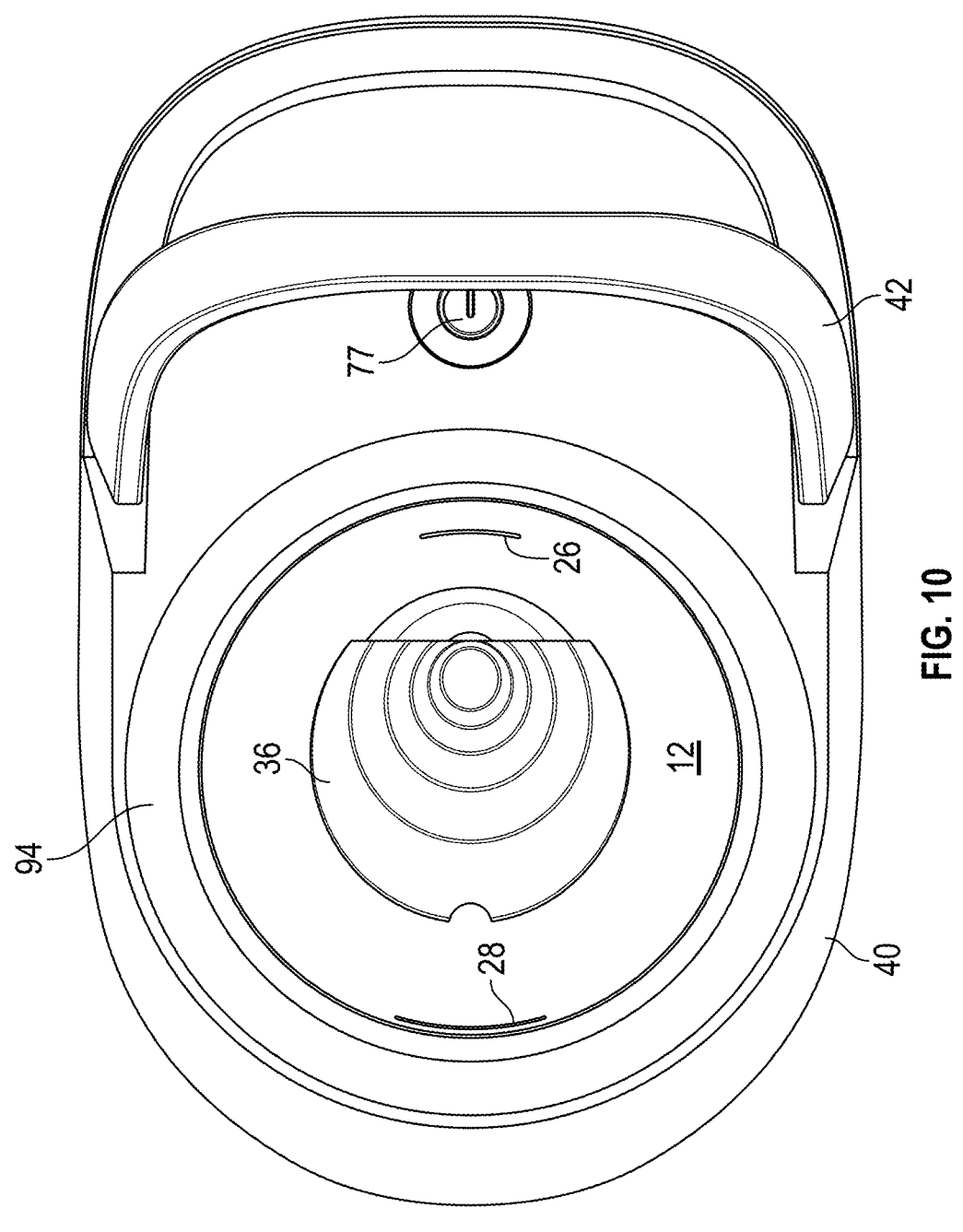
FIG. 10 is a plan view of the flow assembly.

FIG. 7 shows an exploded view of the assembly 10 with the measurement chamber 16 exposed. As shown, the measurement container 15 is essentially three sidewalls that cooperate with the measurement wall 34 to define the measurement chamber 16. The measurement wall may be any object that at least partially contains the fluid in the measurement chamber. FIG. 7 shows the measurement wall 34 and sensors 19 thereon exploded from the main container. The sensors 19 may be sized and/or arranged to allow measurement of the column of fluid in the measurement chamber at any desired level. The sensors 19 may be arranged in a plurality of zones (e.g., twenty nine vertical or vertically staggered sensors 19 that are divided up or arranged into separate measurement zones 46), as shown in FIG. 9 that help identify the level of the fluid. The sensors 19 may include two columns that are staggered left and right. A few exemplary zones 46 are shown in FIG. 9. Any array of zones may be used. For example, the entire array of twenty nine sensors may be a single zone, each sensor may be a zone or the zones represented by numeral 46 in FIG. 9 may be exemplary zones. In another embodiment, the wall 34 and associated sensors 19 may be held in position by a frame.

It will be appreciated that the void container 11 and the void chamber 12 is the volume into which fluid that enters through the upper opening 14 collects, but is separate from the measurement chamber 16 and the overflow chamber 24 (other than any fluid that may enter the overflow tube). As shown in FIG. 3, the exit of the overflow container 23 may be positioned adjacent the exit of the measurement container 15 so fluid that passes through the exit orifice 20 and fluid that passes through the overflow chamber 24 exit a common spout 22. In another embodiment, fluid from the overflow and the exit slot may exit the assembly separately or may be contained in common or separate spaces.

Figure 5:
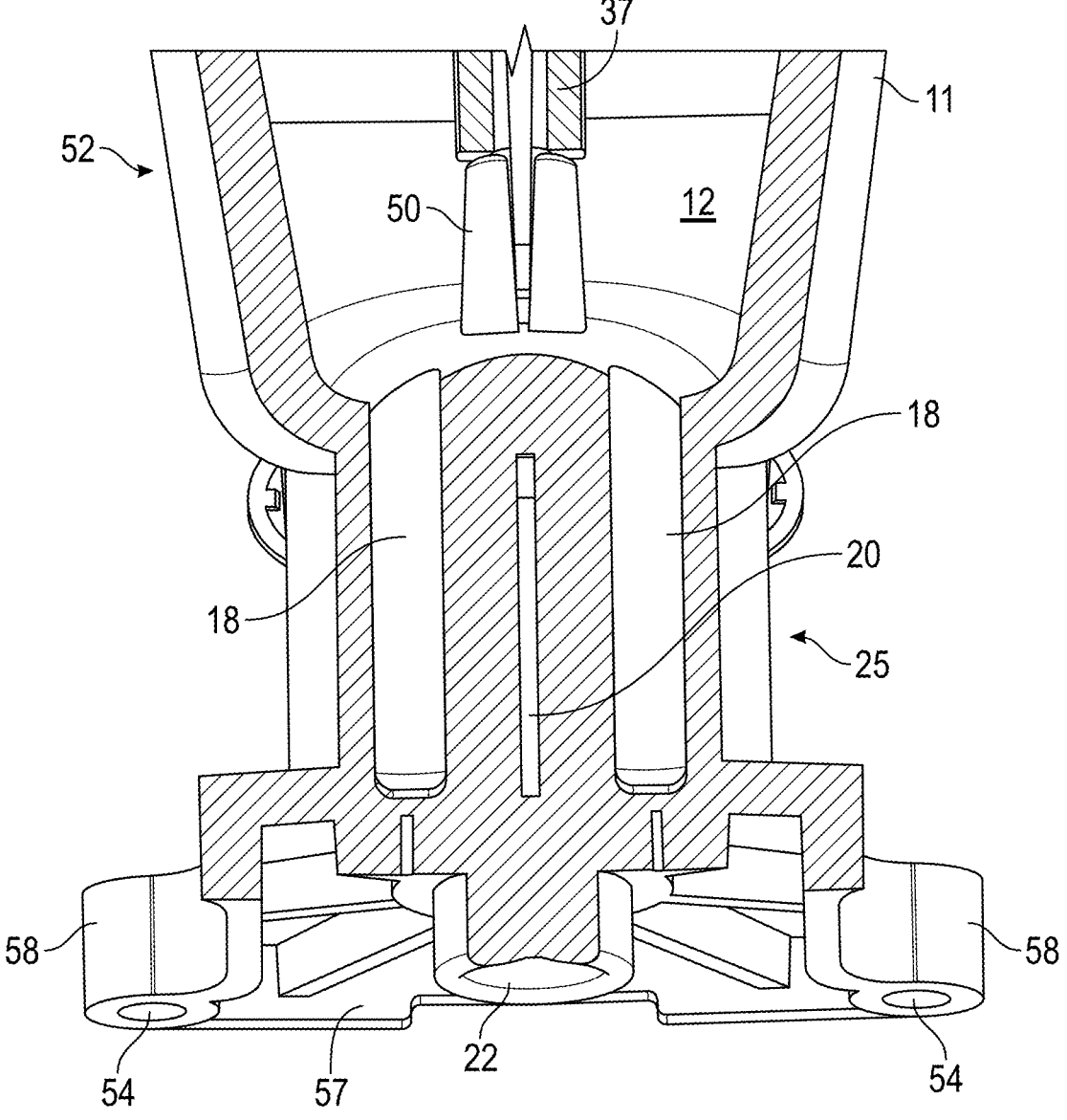
FIG. 5 is a cross-section of a lower portion of the container member showing the exit orifice.

As shown in FIGS. 5 and 8, the measurement chamber 16 includes the exit slot or orifice 20 at or near the bottom thereof. During use, fluid from the measurement chamber 16 continuously drains out of the exit orifice 20. In another embodiment, the exit orifice 20 may be located in or at the bottom of the void chamber 12. It will be appreciated that the shape of exit orifice 20 is important to resolution, accuracy, and precision and low flow rates. For example, in a preferred embodiment, the exit orifice may have a width of between about. 1 mm and a height of about 40 mm or a width of between about 0.5 mm and a height of about 25 mm, or a width of between about 1 mm and a height of about 20 mm, or a width of between about 2 mm and a height of about 10 mm. Any range within the above ranges is also within the scope of the present invention. Any cross-sectional area calculation within these ranges is also within the scope of the present invention. Fluid that has exited the exit orifice 20 (from the measurement container) then drains into and from the spout 22 (and the spout interior 22a) or any opening (which may be directly from the exit slot) that is preferably shaped to direct the fluid out of the device or assembly and into a commode or the like.

In a preferred embodiment, one or more electronic sensors 19 continuously monitor the level of the measurement column in the measurement chamber 16. FIG. 8 shows an example of an array of electronic sensors 19. For example, one or more capacitive sensors may be used, however, this is not a limitation and other types of level-sensors may be used. As shown in FIG. 9, the rectangular extension wall 62 defines an elongated opening 32 that is covered by the measurement wall 34 to at least partially define the measurement container 15 and measurement chamber 16. In a preferred embodiment, the measurement wall 34 may be a rigid PCBA that includes the array of electronic sensors 19 thereon. Preferably, the PCBA includes a coating or coating layer 34a (e.g., a conformal coating) on the inner surface thereof that protects or insulates the electronics of the PCBA or measurement wall from the fluid contained in the measurement chamber 16. For example, the coating layer 34a may be a thin polyimide coating or polyimide prepreg. The thin coating allows the fluid in the measurement chamber 16 to be very close to the sensors 19 on the measurement wall 34, thus allowing accurate measurements and resolution. A variety of coatings may be used for the coating layer 34a.

The polyimide coating may be built into the PCBA or measurement wall 34. Other coatings may include Parlyene, PTFE Duroid, acrylic, silicone, epoxy, etc. or any combination thereof. The entire PCBA may be encapsulated (e.g., via potting or other encapsulation method). The coating may be integrated during the PCB fabrication process using heat and pressure to bond layers, applied via a specialized chemical vapor deposition process after the PCBA is complete, applied via spray, dip, or brush, mixing and pouring a two-part resin or other application process. The coating preferably has low absorption properties that are built into the PCBA substrate itself as a top layer or coating layer 34a. The coating layer 34a may not be completely waterproof, but the low absorption properties allow the signal of the capacitive sensors 19 (i.e., the capsense signal strength) to pass or transmit through the coating layer. For example, the measurement wall 34 may include the PCBA portion, which includes several alternating copper layers and dielectric (prepreg) layers (e.g., four alternating copper layers and four alternating dielectric (prepreg) layers) with a bottom plating layer with the coating layer 34a (e.g., a dielectric polyimide prepreg VT901—the layer that comes into contact with the fluid in the measurement chamber) being opposite the bottom playing layer. Any of the copper and dielectric layers may include one or more through-holes or vias. It will be appreciated that the coating layer 34a is layered on top of the capacitive sensors 19.

In use, the one or more sensors measure the level of the fluid in the measurement chamber 16 during a void event. The array of sensors may include different types of sensors. In an exemplary level measurement process, the measuring process starts with capacitive sensors, then to liquid level sensors, then estimated volume, then estimated flow rate. For example, the method of process may include the following steps: (1) capacitive sensors 19 take raw counts, (2) the counts are translated or converted to a volume measurement that is dependent on the shape of the measurement chamber, void chamber, and the angle (e.g. hang angle) of device, (3) the flow rate is calculated based on the volume from the step above and dependent on the exit slot geometry and the angle of the device. It will be appreciated that during the process, nothing can restrict the flow more than the exit slot geometry for the flow rate to be determined.

Preferably, the capacitive sensors 19 are mounted on or a part of the measurement wall 34 (together with the coating layer 34a-which may also be referred to as a separation layer to separate the fluid from the electronics). Each sensor 19 in the column(s) forms a capacitor with the wall acting as the dielectric. When the fluid level rises to the level of a sensor, it changes the electric field, increasing the capacitance at that point (similar to how a finger affects mutual or self-capacitance in a touchscreen). The system scans the sensors sequentially (much like a touchscreen grid) to detect these changes and determine the fluid level. The plurality of sensors provide discrete (stepped) level measurements. For example, if the bottom three sensors detect high capacitance (indicating fluid presence) while the upper ones do not, the system infers the fluid is at the level of the third sensor. The system continues to monitor the fluid level during a void event as the level may or will change.

During use, each capacitive sensor outputs "raw counts," which are unprocessed digital values from the analog-to-digital converter representing the measured capacitance. For fluid detection, a baseline raw count may be established when the container is empty (low capacitance due to air). As fluid approaches or covers a sensor's level, the raw count increases proportionally (e.g., from 500 to 1500 arbitrary units, depending on the hardware). The controller compares these raw counts against a threshold to determine if fluid is present at that sensor. In the exemplary columnar setup (or dual overlapping columnar setup), an array of raw counts (one per sensor) are "sensed", which the software processes to output the overall level. The system may include a controller or microcontroller or dedicated IC that scans the sensors, processes raw counts, and outputs data. The volume of the measurement container and the volume of the void container is also known or predetermined and may also be calculated based on the hang angle of the device during use (discussed below). Subsets of the volume of the measurement container and the volume of the void container (e.g., the volume at any given level) may also be known.

There may be signal processing as well to clean up any final measurements to establish the flow rate. It will be appreciated that the narrow or small shape and area of the exit orifice 20 allows the fluid that has accumulated in the measurement chamber 16 to exit or flow through and out of the exit orifice at a slow flow rate.

As hydrostatic pressure increases better resolution is provided due to the shape of the exit orifice or window. However, due to this restriction of flow, the measurement assembly 17 preferably also includes an overflow container 23 and overflow chamber 24. In use, should a combination of high flow-rate and/or excessive duration exceed a predetermined capacity of the void chamber 11 together with the measurement chamber 16, the overflow container 23 is provided to direct the excess through an overflow opening 26 in the top of the overflow container 23 (see FIGS. 8 and 10) and to the spout 22. As shown in FIG. 3, the measurement chamber 16 may also include a vent 28 at the top thereof. It should be noted that any entry of fluid into the overflow chamber 24 through the overflow opening 26 invalidates any current test, as the overflow is not be registered by the sensors. Preferably, the overflow cover 35 is secured to a rectangular overflow wall 64 that extends outwardly from the void container 11. The overflow cover 35, rectangular overflow wall 64 and void container 11 together form the overflow container 23 and at least partially define the overflow chamber 24.

Figure 11:
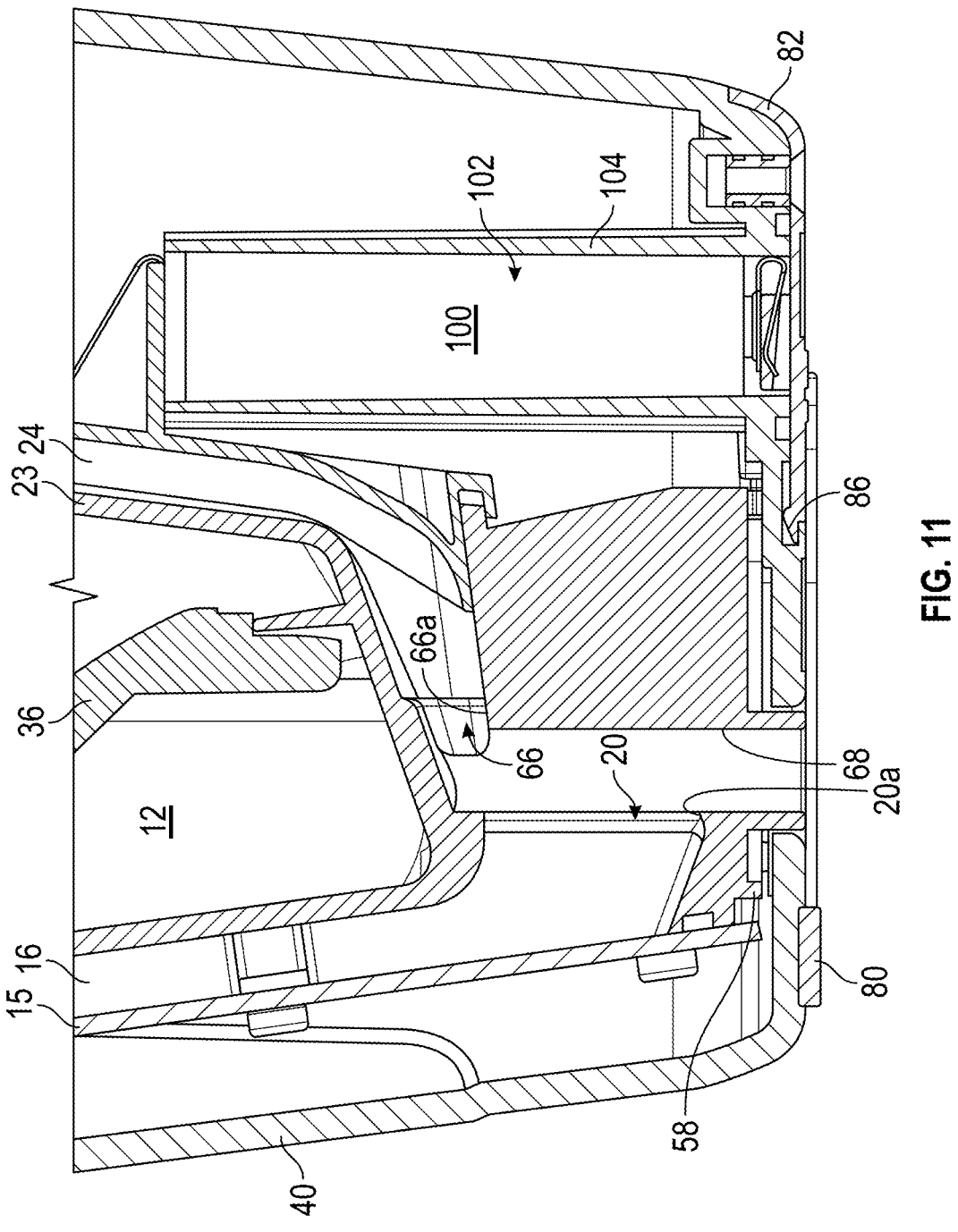
FIG. 11 is a cross-sectional side elevation of the bottom of the flow assembly to show the difference in height of the overflow chamber exit and the measurement container exit.

As shown in FIG. 11, in a preferred embodiment, the bottom surface 66a of the overflow exit 66 is positioned at a level that is above the bottom surface 20a of the exit orifice 20. Preferably, any fluid exiting the overflow exit 66 and any fluid exiting the exit orifice 20 both enter the spout 22 (and the spout interior 22a), thus providing a common spout. However, preferably, the fluid entering the spout the from the overflow exit 66 enters at a level above the exit orifice 20 and, vice versa, fluid entering the spout the from the exit orifice 20 enters at a level below the overflow exit 66. It will be appreciated that the fluid exiting through the exit orifice 20 is preferably laminar and at least not turbulent. Positioning the overflow exit above the exit orifice allows the fluid flowing out of the exit orifice to hit or contact a smooth exit wall 68, thus helping prevent turbulence. The smooth exit wall 68 partially defines the spout interior 22a. In another embodiment, fluid in the overflow chamber may empty or exit through an exit separate from the spout. In a preferred embodiment, the spout 22 is elongated, to allow the overflow exit to be higher than the measurement chamber exit, and rifled to aid in exiting the fluid.

Figure 12:
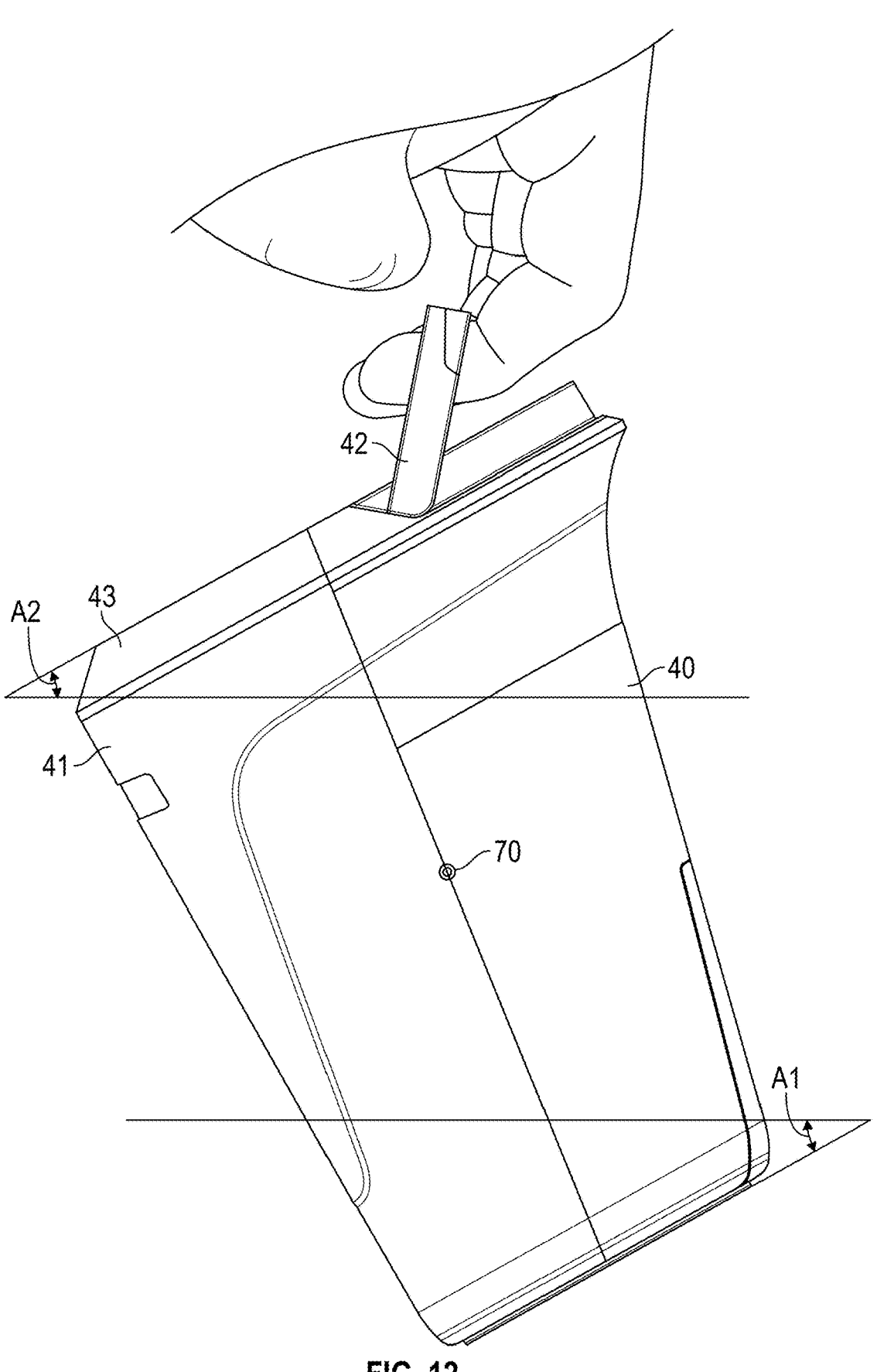
FIG. 12 is an elevational view of the flow assembly showing a user holding the flow assembly at the hang angle.
Figure 13:
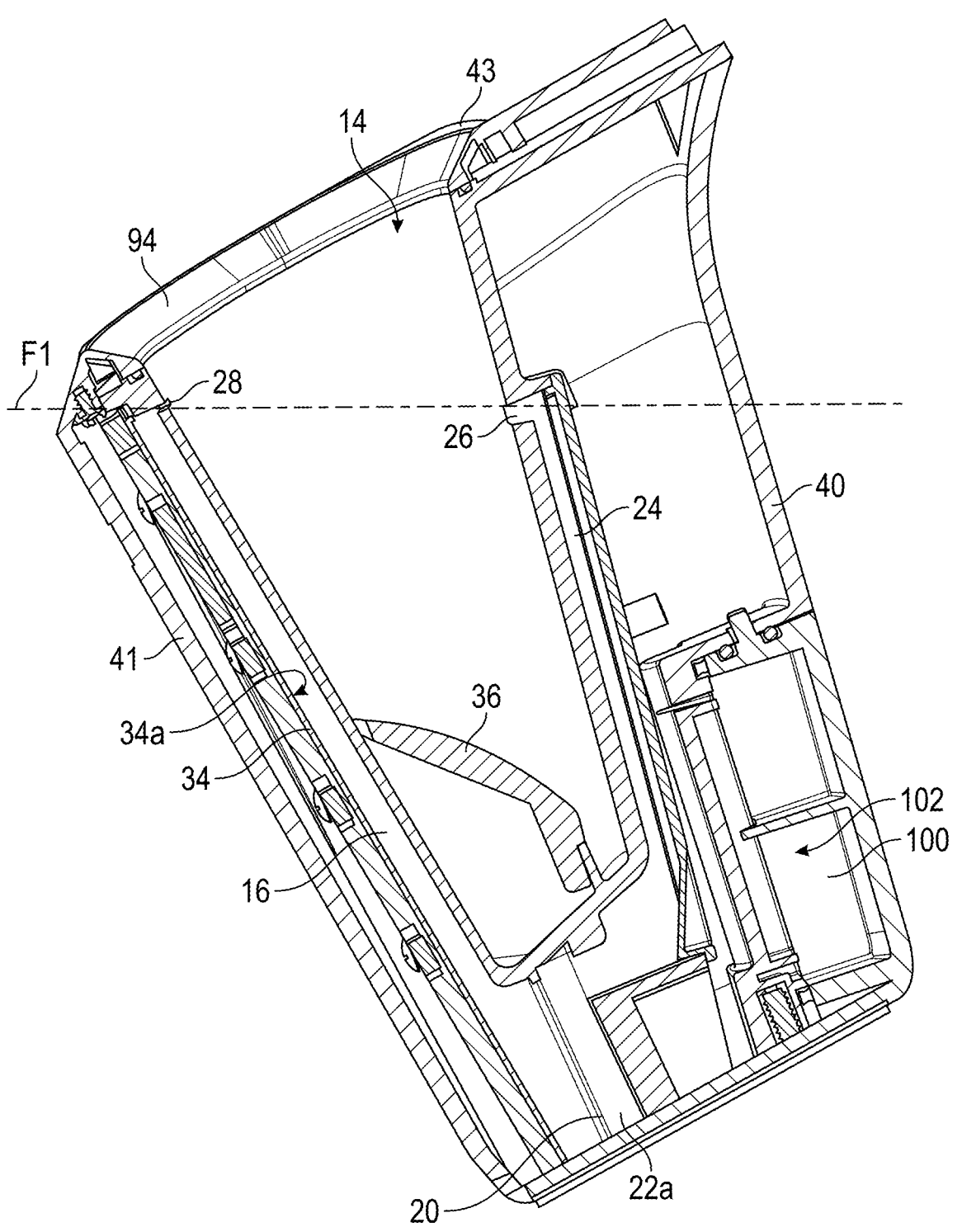
FIG. 13 is a cross-section of the flow assembly oriented at the hang angle.
Figure 14:
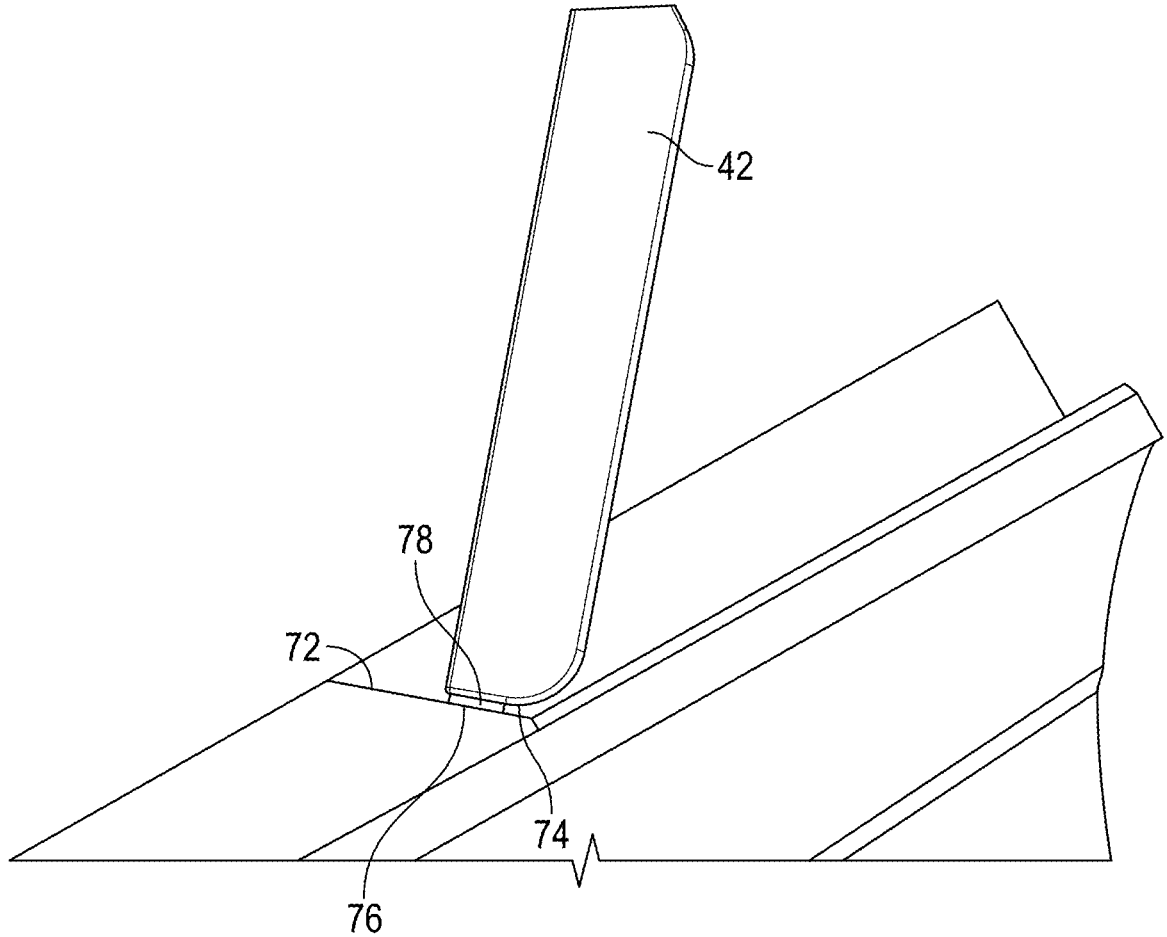
FIG. 14 is a detail view of the handle and related components related to the hang angle.
Figure 15:
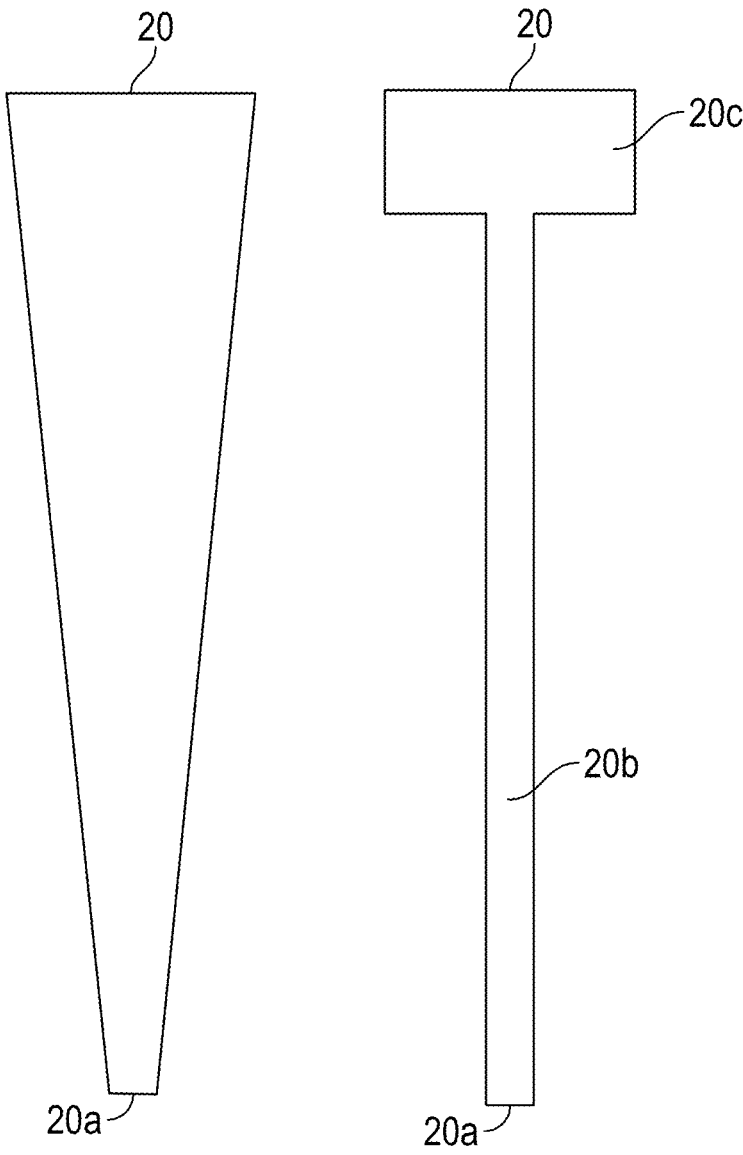
FIG. 15 depicts exemplary shapes of the exit orifice.

With reference to FIGS. 12-14, in a preferred embodiment, during use, the flow measurement assembly or device 10 is positioned at an advantageous hang angle. See the hand holding the handle 42 in FIG. 12, which positions the measurement assembly 17 within the container 40 at the predetermined hang angle. For example, using the horizon as a measurement reference, the bottom surface of the device may form a 22.5 degree angle with the horizon (see the bottom hang angle A1 in FIG. 12) and the top surface of the device may form the same angle or it may be different. For example, in a preferred embodiment, the top surface of the device (e.g., the top surface of the housing) may not be parallel to the bottom surface of the device or housing. In other words, if the bottom surface is resting on a table and is parallel to the table, the top surface may not be parallel to the table or bottom surface. For example, it may be angled downwardly running from the back of the device (where the on/off switch is located) to the front of the device (the measurement chamber side). In an exemplary embodiment, this angle is 7 degrees (the difference between the top surface and the bottom surface). Therefore, returning to the horizon as a reference, the top surface may form a 29.5 degree angle with the horizon (see the top hang angle A2 in FIG. 12). In another embodiment, the top and bottom hang angles may be the same. It will be appreciated that the hang angle (and, in particular, the top hang angle) makes it easier for a user to void into the void chamber. A1 may be any angle between 0 degrees and 45 degrees and more particularly between about 2.5 degrees and 42.5 degrees and A2 may be any angle between 0 degrees and 50 degrees and, more particularly may be between about 9.5 degrees and about 49.5 degrees. The difference between A1 and A2 (described above as 7 degrees as an example) may be any angle between 0 degrees (where A1 and A2 are the same) and about 20 degrees. This angle may be referred to herein as the top slope angle.

In a preferred embodiment, the flow assembly 10 includes one or more of a gyroscope, accelerometer or other measurement or sensing device that is/are associated with an inclinometer so that if the device shakes or moves during use, compensation for the movement can be made and calculated. These components (which may be a part of the main PCB 60) can determine roll, pitch and/or yaw. The inclinometer senses or determines the hang angle (or the top and bottom hang angles) during use. It will be appreciated that the volume of the fluid in the void container and/or measurement container may be calculated based on the hang angle (and/or using the other positioning measurement devices-roll, pitch or yaw). With all of these different measurements, the device can continuously determine the volume within the measurement and void chambers based on the known geometry of the chambers. Thus the flow rate in or inflow calculations can be made and adjusted based on the actual position of the device at any point in time. This provides self-compensating calculations.

In use, when a user holds the device by the handle 42 and allows it hang, the center of gravity 70, together with the angle of the handle causes the housing 40 and other components to be positioned at the predetermined hang angle. The handle 42 is movable between a stowed position (FIG. 1) and a deployed position (FIG. 12). The pivoting of the handle from the stowed position to the deployed position defines a pivot angle. The free ends 74 of the handle each include a contact surface 76 that contacts two stop surfaces 72 on the housing 40, as shown in FIG. 14. In a preferred embodiment, the contact surfaces 76 are part of tabs 78 on the free ends of the handle. In another embodiment, the tabs can be omitted. The angle defined by the stop surfaces 72 and the upper surface of the housing 40 together with the center of gravity cause the housing to hang at the predetermined hang angle (and the top and bottom surfaces at the top and bottom hang angles A1 and A2).

As shown in FIG. 13, a fill line F1 is defined by the hang angle. The overflow opening 26 is defined in the void container 11 at a position such that, when the device is in the hang angle position, fluid will enter the overflow opening 26 before it will enter the vent 28. The hang angle allows the device to automatically compensate for any tilt, pitch, yaw or roll or other change of the device.

It will be appreciated that hydrostatic pressure forces the level in the measurement chamber 16 or measurement column and that in the void chamber 12 to be at or nearly identical or level, even when the device is held at the hang angle.

It will be appreciated that at any point in time during use, the device 10 is or may be computing or determining: instantaneous fluid volume in the device, which may be designated herein as "V", rate-of-change of the measured volume in the device (dV/dt), which may be designated herein as "X", flow-rate exiting the device, as a nonlinear function of V, which may be designated herein as "Y", and volumetric flow rate of the input stream, which is X-Y and may be designated herein as "Z". The device or system is able to translate or convert the geometry of the device (e.g., the known volume of the measurement and void chambers, the hang angle, etc.) to a volume of fluid level. So if the fluid is at a height (i.e., a measured height) the volume of the measurement and void chambers can be determined and the system knows how many "raw counts" are associated with that sensor. Then, because the system knows the size of the exit orifice and the max flow rate that can pass through the exit orifice, raw counts can be associated with volume level, and, as that volume level is shifting (i.e., going up or down) the change in flow rate (or the real time flow rate) can be determined.

An example of a set of steps for the method or use of the flow assembly 10 is presented. The steps may include one or more of the following. A user moves the handle 42 from the stowed position to the deployed position and holds device at the hang angle. The user begins voiding into void chamber 12. Fluid flows through the one or more through-holes 18 after passing or contacting the diverter 36 and enters the measurement chamber 16. The measurement chamber 16 begins filling up as some fluid passes through the exit orifice 20 (the flow rate out is known based on the known size of the exit orifice 20). The measurement chamber 16 and void chamber 12 reach approximately the same level (hydrostatic equilibrium) due to hydrostatic pressure (this happens almost instantaneously. The capacitive sensors 19 determine a first level of fluid at a first point in time. This determination is made based on knowing the counts (a predetermined number of counts). The flow assembly calculates a first volume of fluid (at the first point in time) based on the level determined by the sensors 19 and knowing the geometry of the measurement chamber 16 and void chamber 12. The capacitive sensors 19 determine a second level of fluid at a second point in time. This determination is made based on knowing the counts (a predetermined number of counts). The flow assembly calculates a second volume of fluid (at the second point in time) based on the level determined by the sensors 19 and knowing the geometry of the measurement chamber 16 and void chamber 12. The flow rate in is then determined based on the time difference between the first and second points in time. Flow rate in equals (volume at the second time minus the volume at the first point in time) minus flow rate out times the difference in time between the first and second points in time, divided by the difference in time between the first and second points in time.

The method may also include the following steps or considerations: (1) The liquid level sensors 19 (capacitive pads) take counts; (2) The counts translate to a fluid volume inside the device. This translation is dependent on the common chamber's (the combined measurement and void chambers) shape (i.e., dimensions) and orientation (as determined by the position sensors, such as the inclinometer(s), gyroscope(s) and/or accelerometer(s)); (3) The flow rate out is calibrated at every volume level dependent on exit slot geometry; (4) flow rate in is a function of the volume change over time and flow rate out; and (5) during the void event and flow rate in measurement, nothing can restrict the fluid flow more than the exit slot geometry.

For example, during a void event, two or more volumetric measurements may be taken to determine flow rate in. Here we use only two measurements. For the first level measurement, the liquid level sensor count at a first predetermined or point in time is 800, which equals a volume of 50 ml (Device Volume$_1$). A second level measurement is taken 0.2 seconds ($\Delta$Time) later and the liquid level sensor count is 900, which equals a volume of 52 ml (Device Volume$_2$). The flow rate out is 10 ml/s, based on the size of the exit orifice. Device Volume$_2$=Device Volume$_s$+Fluid Volume$_{In}$+Fluid Volume$_{Out}$. Volume to flow rate conversion. Fluid Volume$_{In}$=Flow Rate$_{In}$×Time. Fluid Volume$_{Out}$=Flow Rate$_{Out}$×Time.

$$\frac{(\text{Device Volume2} - \text{Device Volume1}) + \text{Flow } RateOut \times \Delta \text{ Time}}{\Delta\text{Time}} = \text{Flow } RateIn$$

$$\frac{(52 \text{ ml} - 50 \text{ ml}) + 10 \text{ ml/s} \times 0.2 \text{ s}}{0.2 \text{ s}} = 20 \text{ ml/s}$$

It will be appreciated that there are a number of static known conditions for the flow rate in determination, including the geometries of the measurement and void chambers (e.g., volume, cross-sectional area at each level, surface area of the walls, etc.), the LLS or liquid level sensor counts (to convert to volume) and the flow rate out (due to the known dimensions of the exit orifice). The only thing changing during the test is the flow rate in. If the flow rate in is decreasing the volume will drop and you get a lower count on the liquid level sensor(s) (LLS) and vice versa. The system or device knows the counts for each volume. All sensors in the array may be considered a single liquid level sensor. In use, the system is taking continuous readings to develop a graph or curve. For example, the system may take readings as often as a 0.05 seconds. It will be appreciated that there is a minimum flow rate that is needed to allow the measurement chamber to begin to fill up. For example, the exit orifice may be sized so that any flow rate in greater than 2.5 ml/s allows the measurement chamber to begin filling up so that measurements can be taken.

Figure 16:
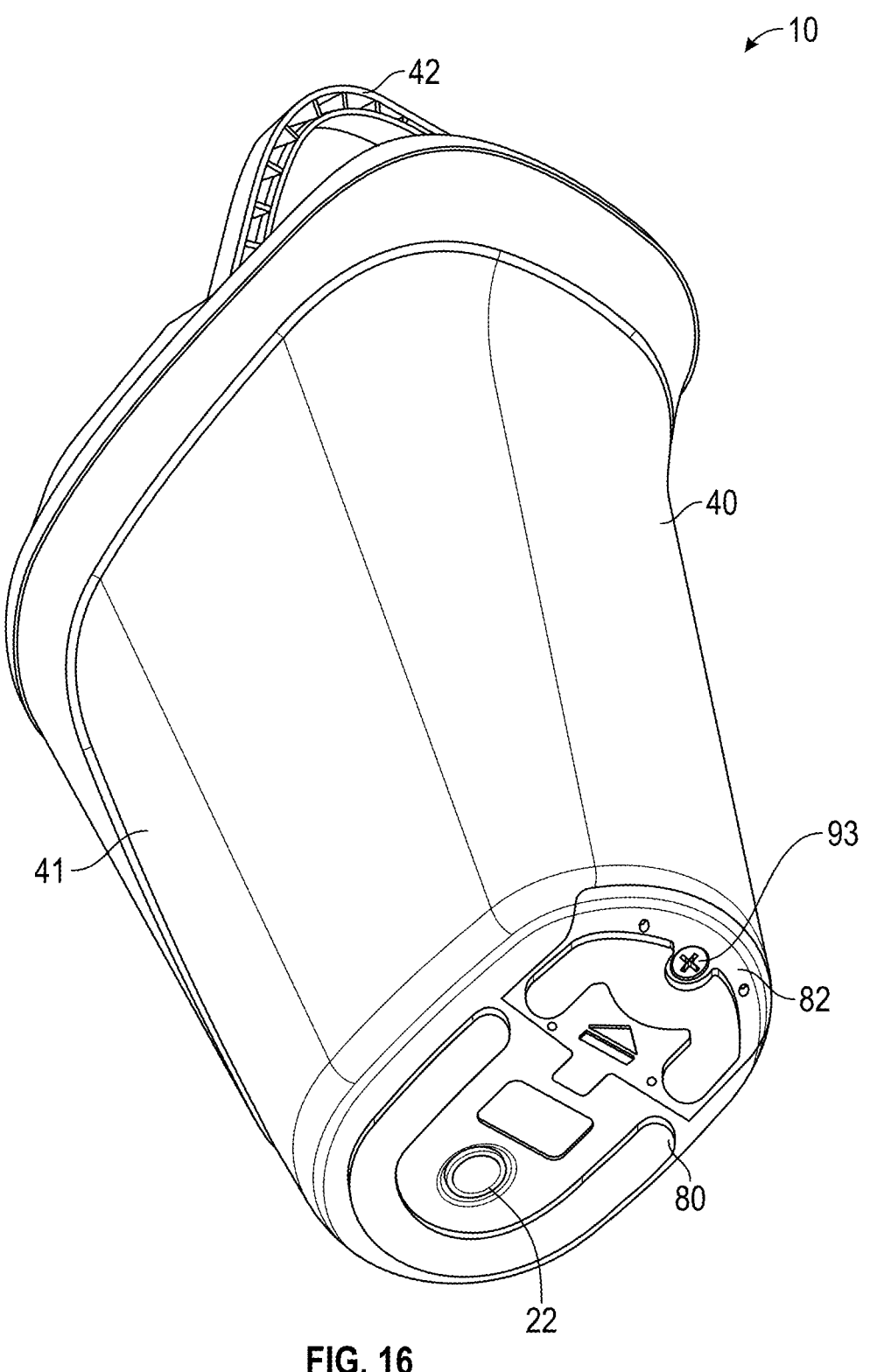
FIG. 16 is a bottom perspective of the flow assembly.

It will be appreciated that fluid exits faster through the exit orifice 20 as the measurement chamber 16 fills due to increased hydrostatic pressure. In a preferred embodiment, the exit orifice is rectangular, as discussed above and the constant dimension of the rectangular shape provides good resolution as hydrostatic pressure increases (and the fluid level increases. However, at high flow rates, because the rectangular shape restricts flow, the void chamber and measurement chamber may fill up high enough that the overflow opening is reached, thereby invalidating the measurement. To help with this issue, in another embodiment, the exit orifice may include a portion thereof that includes a larger horizontal cross-section above the bottom edge or surface of the exit orifice. For example, the exit orifice may be V-shaped or T-shaped, as shown in FIG. 16, which may be advantageous for higher flow rates, while maintaining acceptable accuracy. The V-shape has a first horizontal dimension or width at the bottom edge (e.g., 1.0 mm) and a second horizontal dimension or width at the top edge (e.g., 2.0 mm) with the dimension of slope increasing at a constant from the bottom to the top. A trapezoid shape may also be used with the smaller dimension at the bottom. The T-shape includes a constant horizontal dimension or width in a bottom section or zone 20b and a second horizontal dimension or width in an upper section or zone 20c. With the V or T-shape the overflow may be omitted. For example, for the T-shape, the bottom section or zone 20b may be within the ranges described herein with respect to the rectangular shaped exit orifice and the upper section or zone 20c may have a width that is wider than the bottom section and may be anywhere between two to ten times wider than the bottom section. For the V-shape, the bottom surface 20a (the bottom of the V) may have a width within the ranges described herein with respect to the rectangular shaped exit orifice and widen upwardly such that the top surface has a width that is anywhere between 1.5 to 10 times wider than the bottom surface.

It will be appreciated that the housing 40 surrounds or encompasses many of the components discussed herein, including the measurement assembly 17. As shown in FIG. 13, the assembly 10 may also include indicators or lights that may provide further information regarding the results of a test. For example, a light ring 94 around the top of the upper opening 14 may be green to indicate great flow, yellow to indicate moderate flow, red to indicate unhealthy flow or blue to show the device is in standby mode. The light ring 94 may include a plurality of lights 44 (e.g., LEDs shown on a PCB in FIG. 3) that are positioned under the angled surface (e.g., an angled light surface 94a). Any colors, lights or locations of the lights or other indicators are within the scope of the present invention. These indicators and the numbers associated with great, moderate, unhealthy flow, etc. may be based upon known medical assessments or calculations. The flow assembly 10 includes an on/off switch or button 77 that may also be used to cycle through modes (e.g., multiple pushes or long pushes). The button 77 may be mounted on the same PCB as the lights 44 or may be included on another surface of the housing.

Figure 17:
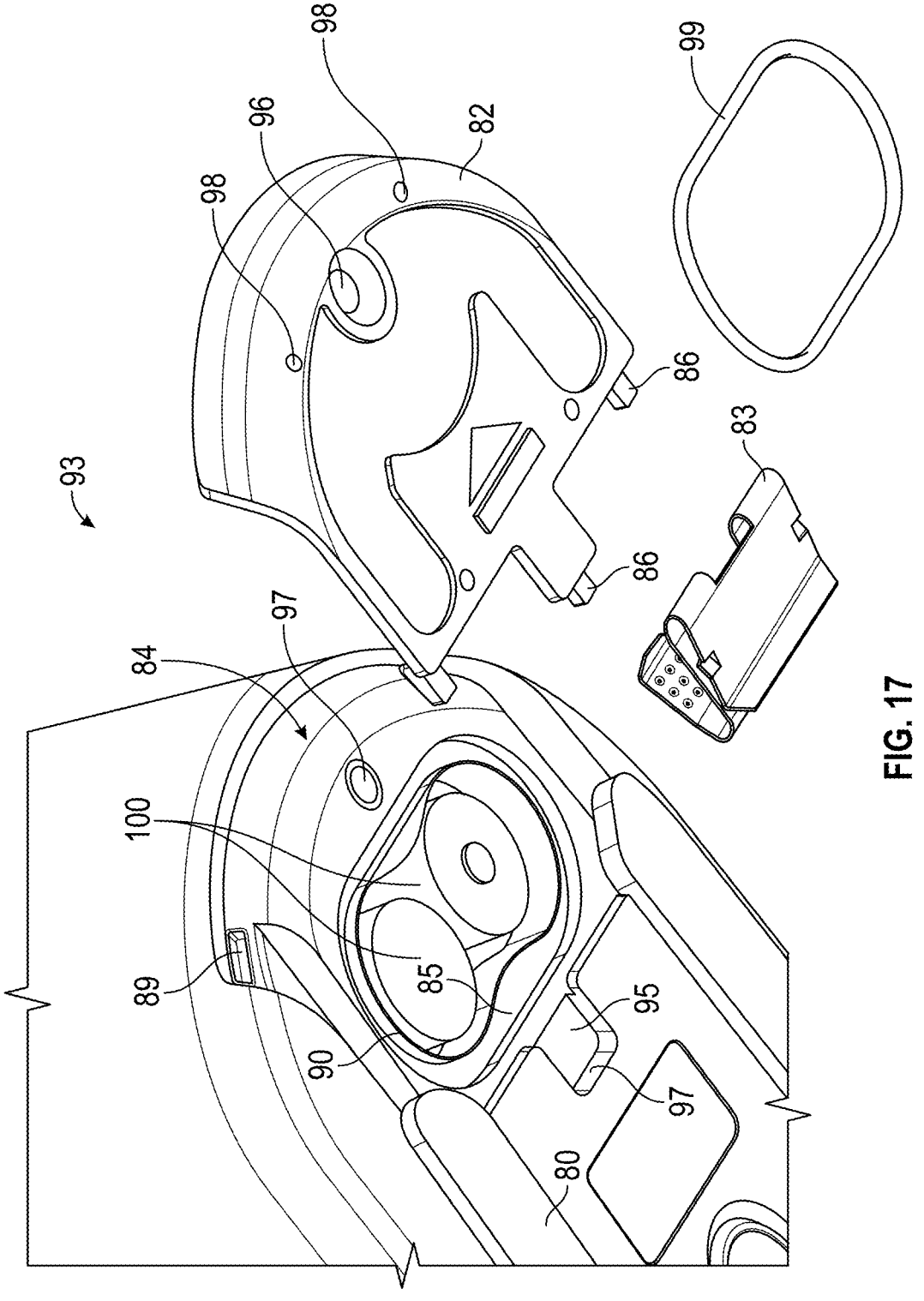
FIG. 17 is an exploded perspective view of the battery door assembly.
Figure 18:
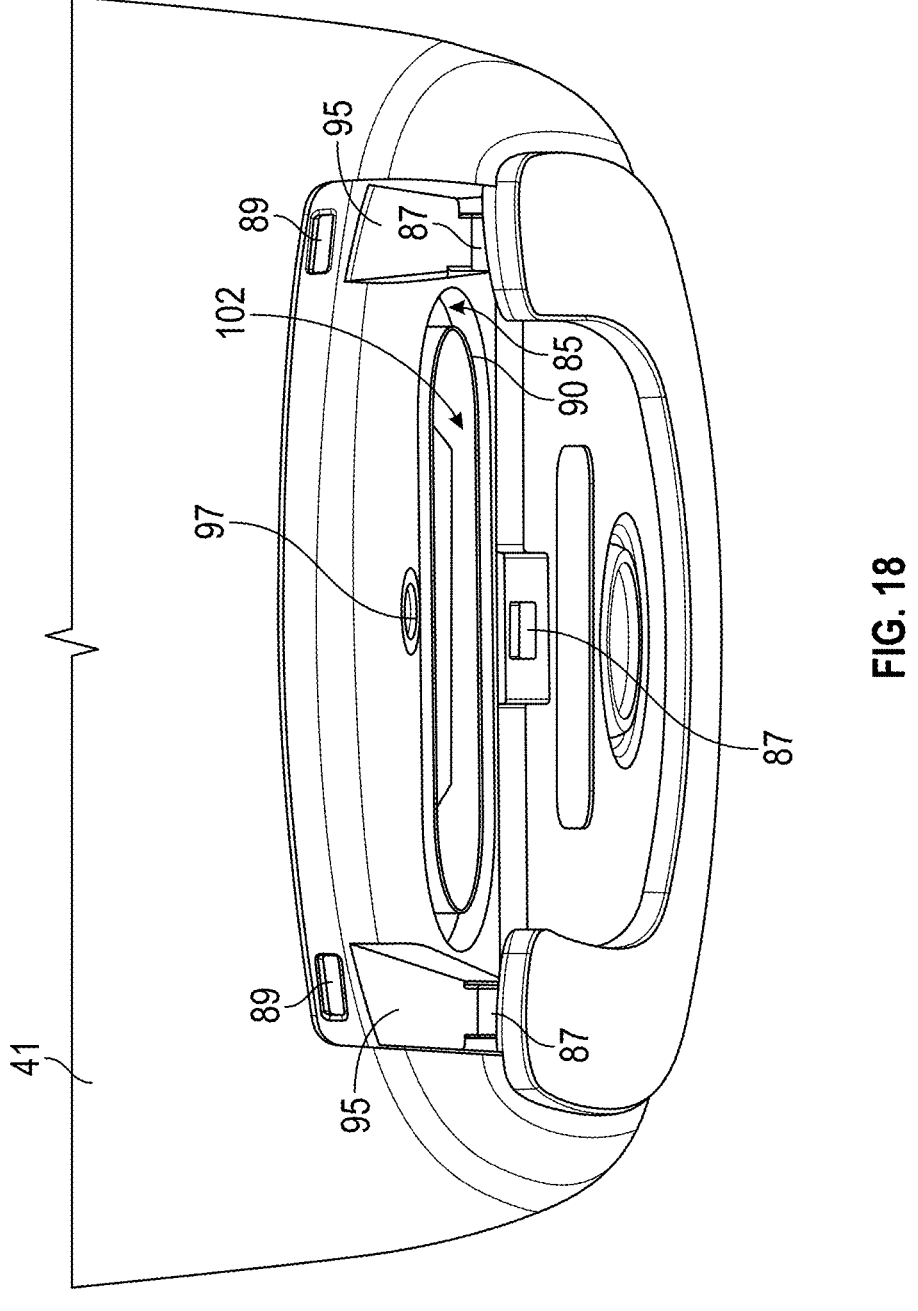
FIG. 18 is a rear perspective view of the bottom of the flow assembly with the battery door removed.
Figure 19:
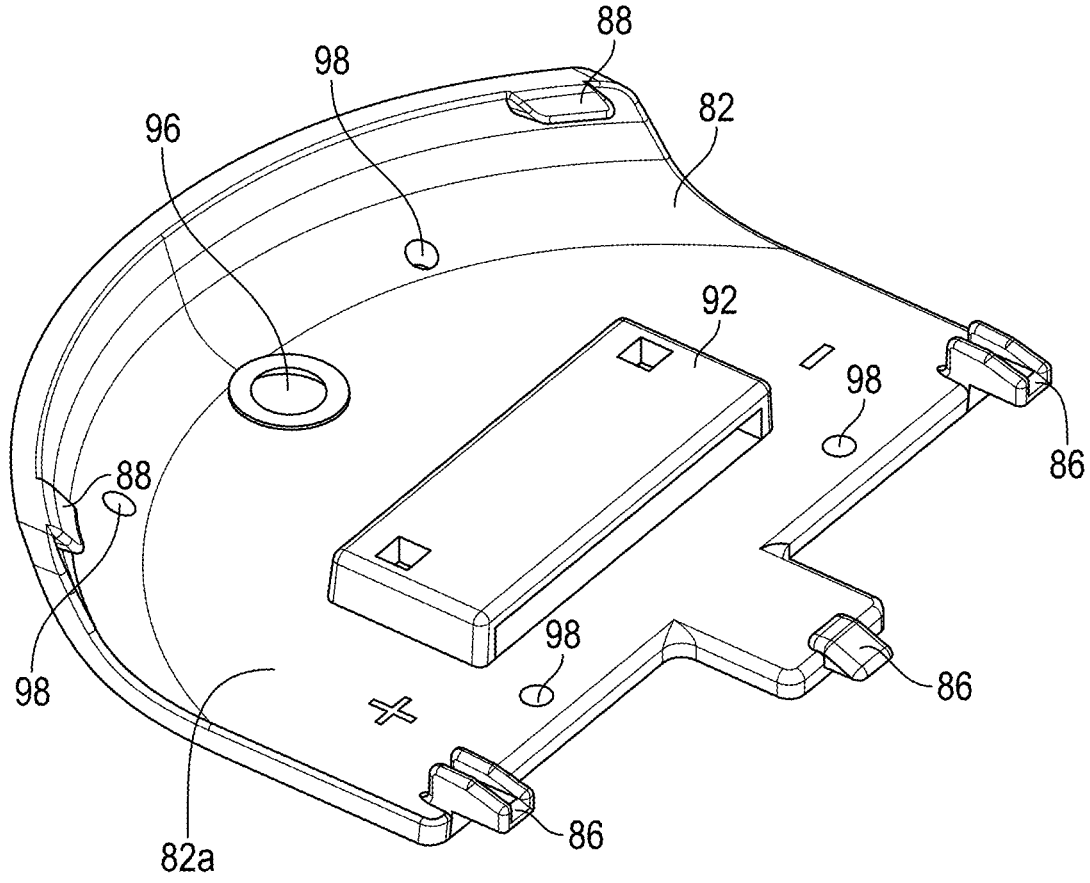
FIG. 19 is a perspective view of the battery door.

FIGS. 16-19 show the bottom of the flow assembly 10 and the various components thereof. In a preferred embodiment, the housing 40 includes a grip foot (or feet) or pad member 80 (or pad members) thereon that at least partially surrounds the spout 22, which protects the bottom surface of the spout 22 from contacting the surface on which the pad member may rest when the device is not in use. The batteries 100, battery door 82, battery spring 83 and related components are also shown. Preferably, battery door assembly 93 is waterproof. The battery door assembly 93 includes or may include the battery door 82, door recess 84, battery flange member 90, gasket trough 85 and gasket 99. The batteries 100 (e.g., AA batteries) extend into and are received in one or more battery compartments 102 that are defined by a battery containment housing 104 (see FIG. 11) that are defined in and from the bottom wall of the main body portion 41 of the housing 40. Preferably, the batteries 100 are oriented in a side by side orientation where they are inserted in an axial direction, as shown in FIG. 17. In a preferred embodiment, the battery door 82 includes five tabs and mating tab receivers. As shown in FIGS. 18 and 19, the five tabs include three lower tabs 86 and two upper tabs 88, as well as mating three lower tab receivers 87 and two upper tab receivers 89. Channels 95 may also be provided for providing clearance for the lower tabs 86 when the battery door 82 is connected.

The battery door 82 preferably includes a first fastener opening 96 that receives a threaded fastener 93 or the like that is retained in a second fastener opening 97 in the housing 40, to help maintain the door in place and pull the gasket 99 against the door to provide waterproofing. A spring receiving platform 92 may also be included on the inner surface of the battery door 82 onto which the battery spring 83 is mounted. The battery spring 83 is sized to fit into the battery compartment 102 such that it pushes against the batteries 100 to provide an electrical connection or circuit. The gasket 99 positioned in the gasket trough 85 seals against the inner surface 82a of the battery door 82. In use, the lower tabs 86 are inserted into channels 95 and are slid or moved into lower tab receivers 87. The upper tabs are received in upper tab receivers 89 and the battery spring 83 and spring receiving platform (or at least a portion thereof) is received in the battery compartment 102. The threaded fastener 91 is then inserted through and into the first and second fastener openings 96 and 97 to secure the battery door 82 in place and compress the door against the gasket to seal the battery compartment(s) 102. The battery door 82 may also include one or more weep holes 98 (four are shown in FIG. 19) to allow for moisture to escape.

In a preferred embodiment, the flow assembly 10 may include further electronic features, such as wireless connectivity (e.g., Bluetooth, WiFi, etc.). The assembly 10 may include connectivity to a software application ("app") that allows the device to operated, controlled or the like via a user's mobile device, such as a cellphone. Data from the assembly 10 may be communicated to the app, which may put the data and other information into usable or displayable form for the user (e.g., tables, charts, etc.).

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A flow measurement device for assessing free surface fluid flow, comprising: a void container defining a void chamber and including an upper opening configured to receive the free surface fluid flow, a measurement container defining a measurement chamber in fluid communication with the void chamber via at least one through opening, an exit orifice defined in the measurement container and configured to allow fluid to drain from the measurement chamber at a known outflow rate based on fluid level, at least one capacitive sensor configured to measure a level of fluid in the measurement chamber, wherein the capacitive sensor is arranged on a measurement wall that at least partially defines the measurement chamber, wherein the measurement wall includes a coating layer on an inner surface thereof to insulate the capacitive sensor from fluid while allowing capacitive measurement through the coating layer, a processor configured to calculate an inflow rate of the free surface fluid flow based on a rate of change in fluid volume derived from the measured fluid level and the known outflow rate through the exit orifice, a diverter positioned in the void chamber above the at least one through opening to prevent direct entry of fluid into the at least one through opening and isolate the measurement chamber from splashing or turbulence in the void chamber, an outer housing enclosing the void chamber and measurement container, a handle pivotally attached to the outer housing and movable between a stowed position and a deployed position to position the device at a predetermined hang angle during use, wherein the predetermined hang angle positions a top surface of the device at an angle between about 9.5 degrees and about 49.5 degrees relative to horizontal, and at least one of an inclinometer, gyroscope, or accelerometer configured to detect the hang angle and adjust volume calculations based on device orientation, including roll, pitch or yaw, wherein a fluid path is defined through the upper opening, into the void chamber, through the at least one through opening, into the measurement chamber, and through the exit orifice.

2. The flow measurement device of claim 1, further comprising an overflow container defining an overflow chamber in fluid communication with the void chamber via an overflow opening positioned to receive excess fluid when a capacity of the void chamber and measurement chamber is exceeded, and a spout in fluid communication with both the exit orifice and an exit of the overflow chamber, wherein the exit of the overflow chamber is positioned above the exit orifice.

3. The flow measurement device of claim 1, further comprising indicators configured to provide feedback on flow rate.

4. The flow measurement device of claim 1, wherein the free surface fluid flow is urinary flow.

5. The flow measurement device of claim 3, wherein the indicators include a light ring around the upper opening displaying colors indicative of flow quality.

*    *    *    *    *